United States Patent
Lee et al.

(10) Patent No.: US 12,373,962 B2
(45) Date of Patent: Jul. 29, 2025

(54) APPARATUS AND METHOD FOR GENERATING THREE-DIMENSIONAL MODEL THROUGH DATA MATCHING

(71) Applicant: MEDIT CORP., Seoul (KR)

(72) Inventors: Dong Hoon Lee, Goyang-si (KR); Myoung Woo Song, Seoul (KR)

(73) Assignee: MEDIT CORP., Seoul (KR)

( * ) Notice: Subject to any disclaimer, the term of this patent is extended or adjusted under 35 U.S.C. 154(b) by 106 days.

(21) Appl. No.: 17/858,091

(22) Filed: Jul. 6, 2022

(65) Prior Publication Data

US 2022/0338738 A1    Oct. 27, 2022

Related U.S. Application Data

(63) Continuation of application No. PCT/KR2021/000208, filed on Jan. 7, 2021.

(30) Foreign Application Priority Data

Jan. 7, 2020 (KR) .................. 10-2020-0002044

(51) Int. Cl.
   *G06T 7/33* (2017.01)
   *A61B 5/00* (2006.01)
   (Continued)

(52) U.S. Cl.
   CPC .............. *G06T 7/33* (2017.01); *A61B 5/0088* (2013.01); *A61B 5/4547* (2013.01); *H04N 13/111* (2018.05); *H04N 13/218* (2018.05)

(58) Field of Classification Search
   CPC ............. G06T 2207/30036; G06T 7/33; G06T 2207/10028; G06T 17/20; H04N 13/218;
   (Continued)

(56) References Cited

U.S. PATENT DOCUMENTS 10,839,481 B1 *  11/2020  Chen ................... G06T 7/344
2004/0029068 A1 *  2/2004  Sachdeva ............ G16H 50/50
                                                        433/24
(Continued)

FOREIGN PATENT DOCUMENTS

JP    2019-051323 A    4/2019
KR    10-2014-0105473 A    9/2014
(Continued)

OTHER PUBLICATIONS

International Search Report mailed Apr. 8, 2021 for International Application No. PCT/KR2021/000208 and its English translation.
(Continued)

*Primary Examiner* — Rowina J Cattungal
(74) *Attorney, Agent, or Firm* — Insight Law Group, PLLC; Seung Lee

(57) ABSTRACT

A method for generating a three-dimensional model through data matching according to an embodiment of the present disclosure comprises: a maxillary scanning step of acquiring maxillary oral data including maxillary teeth by scanning the maxilla of a patient by using an oral scanner, a mandibular scanning step of acquiring mandibular oral data including mandibular teeth by scanning the mandible of the patient by using the oral scanner, an occlusion step of acquiring occlusal oral data in a state in which the maxillary teeth and the mandibular teeth are occluded, by using the oral scanner; a face scanning step of acquiring first facial data by scanning a face of the patient by using the oral scanner; and a matching step of matching the first facial data with at least one of the maxillary oral data, the mandibular oral data, and the occlusal oral data.

11 Claims, 17 Drawing Sheets

(51) Int. Cl.
*H04N 13/111* (2018.01)
*H04N 13/218* (2018.01)

(58) Field of Classification Search
CPC ..... H04N 13/111; A61C 19/05; A61C 9/0046; A61B 5/0088; A61B 5/4547
See application file for complete search history.

(56) References Cited

U.S. PATENT DOCUMENTS

| | | | |
|---|---|---|---|
| 2004/0197727 A1* | 10/2004 | Sachdeva | A61C 7/00 433/24 |
| 2005/0271996 A1* | 12/2005 | Sporbert | A61C 7/00 433/24 |
| 2014/0242539 A1 | 8/2014 | Fisker et al. | |
| 2014/0372084 A1* | 12/2014 | Cowburn | A61C 13/0004 703/1 |
| 2014/0379356 A1* | 12/2014 | Sachdeva | A61C 7/002 705/2 |
| 2019/0216580 A1 | 7/2019 | Fisker et al. | |
| 2019/0254789 A1 | 8/2019 | Lancelle et al. | |
| 2021/0241885 A1* | 8/2021 | Ouyang | G16H 50/20 |

FOREIGN PATENT DOCUMENTS

| | | |
|---|---|---|
| KR | 10-2017-0125599 A | 11/2017 |
| KR | 10-2017-0135857 A | 12/2017 |
| KR | 10-1840444 B1 | 3/2018 |
| KR | 10-2018-0126015 A | 11/2018 |

OTHER PUBLICATIONS

Bechtold T E et al: "Integration of a maxillary model into facial surface stereophotogrammetry ; Uber die Integration des Kiefermodells in die Oberflachen-Stereofotogrammetrie des Gesichtes", Journal of Orofacial Orthopedics / Fortschritte Deer Kieferorthopadie, Urban & Vogel, MU, vol. 73, No. 2, Mar. 2, 2012 (Mar. 2, 2012), pp. 126-137, XP035029466.

Extended European Search Report mailed on Dec. 18, 2023 from the European Patent Office for European Application No. 21738175.5.

Non-final Office Action mailed on Dec. 22, 2023 from the Korean Intellectual Property Office for Korean Application No. 10-2020-0002044.

* cited by examiner

APPARATUS AND METHOD FOR GENERATING THREE-DIMENSIONAL MODEL THROUGH DATA MATCHING

CROSS-REFERENCE TO RELATED APPLICATIONS

This application is a continuation application of International Application No. PCT/KR2021/000208, filed Jan. 7, 2021, which claims the benefit of Korean Patent Application No. 10-2020-0002044, filed Jan. 7, 2020 in the Korean Intellectual Property Office, the disclosures of which are incorporated herein in their entirety by reference.

TECHNICAL FIELD

The present disclosure relates to an apparatus and method for generating a three-dimensional model through data matching, and more specifically, to an apparatus and method for generating a three-dimensional model through data matching, which generate the three-dimensional model by generating and matching facial data, maxillary/mandible oral data, and occlusal oral data of a patient using an oral scanner.

BACKGROUND ART

A dental prosthesis manufacturing process includes a process of manufacturing an accurate prosthesis based on the corresponding tooth information by acquiring information on patient's teeth. Conventionally, impressions are taken on teeth and gums using an impression material on the patient's teeth, and a plaster is manufactured after taking the impressions, and a prosthesis is produced based on the corresponding plaster.

However, in the conventional process, there is a difference in accuracy depending on the skill levels of the operators (dentist or dental workers), and the patient's rejection reaction (vomiting, discomfort, or the like) may occur in a process of inserting the impression material into the patient's oral cavity. In addition, since a manual process from taking impressions to manufacturing the prosthesis is added, there is a disadvantage in that it is expensive and takes a long time.

Accordingly, recently, methods of manufacturing the prostheses based on dental computer aided design/computer aided manufacturing (CAD/CAM) technologies that uses an oral scanner to generate a virtual three-dimensional model for the shape of the patient's affected area, such as teeth, gums, and jawbone are constantly being developed.

Using three-dimensional data acquired for the patient's affected area, prosthetic treatment, orthodontic treatment, or the like may be accurately calculated and performed using a computer. At this time, to obtain good treatment results, it is necessary to secure three-dimensional data that accurately reflects the shape of the patient's affected area.

Medical devices such as computed tomography (CT) and magnetic resonance imaging (MRI) may be used to obtain the three-dimensional data of the affected area in a dental CAD/CAM treatment process. For example, medical devices such as X-ray computed tomography (CT) such as cone beam computed tomography (CBCT) and magnetic resonance imaging (MRI) may be used to acquire volumetric data expressed in the form of having an intensity value within a voxel structure.

The volumetric data acquired by the CT or the like has an advantage in that it may also express not only the shape of externally exposed surfaces such as teeth and gums, but also the internal shape of the patient's affected area not externally exposed such as a tooth root or a jawbone.

However, it is known that the dental treatment requires an accuracy of 0.05 mm or less to manufacture a prosthesis suitable for the patient's affected area, and the accuracy of CT data is about 0.2 mm, which does not satisfy the requirements for the dental treatment, so that there are restrictions on the use of the dental treatment.

In the dental CAD/CAM field, optical three-dimensional scanners in addition to the CT are widely used. The optical three-dimensional scanner may acquire three-dimensional surface shape information of a target to be measured, and for example, may acquire three-dimensional data for an impression body of the patient's oral cavity or teeth, a plaster 모델 acquired with the impression body, and the like.

In particular, there are advantages in that various dental treatments and treatment plans may be established, treatment costs may be saved and treatment times may be reduced, and the patient's rejection reaction may be reduced by using the oral scanner.

In addition, the three-dimensional surface data acquired by using the optical three-dimensional scanner for dental CAD/CAM is known to have a relatively high accuracy (e.g., about 20 um or less), and has a relatively high accuracy of about 60 um even when the whole subsequent processing is included. In applications using the dental CAD/CAM, the surface data is used for various purposes.

Meanwhile, more accurate treatment may be performed in the process of manufacturing or correcting the prosthesis when additional patient information is acquired in addition to the patient's oral data than when only the patient's affected area data acquired by the oral scanner is used, and two-dimensional image data such as X-rays or patient's photos are mainly used.

However, since it is difficult to understand the relationship with virtual model data for the patient's affected area with two-dimensional images such as X-rays or patient's photos, dental experts check the virtual model data with the naked eye and only use it as an auxiliary for the patient's dental treatment.

Accordingly, there are restrictions in that it is difficult to be used to determine an insertion direction of an implant or design a prosthesis in consideration of information such as the shapes of the teeth around the missed affected area and the face area around the teeth when planning implant surgery using only the two-dimensional images such as X-rays or patient's photos.

Accordingly, integrated three-dimensional data for the entire maxilla/mandibular area of the patient such as the patient's face around the teeth, as well as the teeth is needed to check the states of the shapes of the teeth and the face before treatment and predict expected changes after treatment during the treatment of diseases or orthodontic treatment related to teeth and jawbone.

SUMMARY OF INVENTION

Technical Problem

An object of the present disclosure is to provide an apparatus and method for generating a three-dimensional model through data matching, which provide information that enables more accurate treatment for prosthesis manufacturing or orthodontics through multiple data matching based on facial data, maxillary/mandibular oral data, and occlusal oral data of a patient acquired by an oral scanner, and a recording medium.

In addition, another object of the present disclosure is to provide an apparatus and method for generating a three-dimensional model through data matching, which provide integrated three-dimensional data for the entire maxillary/mandibular area of a patient such as the patient's face as well as teeth by additionally providing information acquired by an extraoral scan together with oral data for the patient's affected area acquire by an oral scanner, and a recording medium.

In addition, still another object of the present disclosure is to provide an apparatus and method for generating a three-dimensional model through data matching, which may easily check states of shapes of teeth and a face before treatment and predict expected changes after treatment during the treatment of diseases or orthodontic treatment related to teeth and jawbone, and may be used to determine an insertion direction of an implant or design a prosthesis in consideration of shapes of teeth and a face around a missed affected area when planning implant surgery, and a recording medium.

The objects of the present disclosure are not limited to the above-described objects. Other objects not mentioned will be clearly understood to those skilled in the art to which the present disclosure pertains from the following description.

Solution to Problem

A method of generating a three-dimensional model through data matching according to an embodiment of the present disclosure includes: a maxilla scanning operation of acquiring maxillary oral data including maxillary teeth by scanning a patient's maxilla using an oral scanner; a mandible scanning operation of acquiring mandibular oral data including mandible teeth by scanning the patient's mandible using the oral scanner; an occluding operation of acquiring occlusal oral data in a state in which the maxillary teeth and the mandibular teeth have been occluded using the oral scanner; a face scanning operation of acquiring first facial data by scanning the patient's face using the oral scanner; and a matching operation of matching the first facial data with at least one among the maxillary oral data, the mandibular oral data, and the occlusal oral data.

The matching operation may include: a teeth data extracting operation of extracting teeth data corresponding to a part of the patient's teeth from the first facial data; a first matching operation of matching the teeth data with at least one of the maxillary oral data and the mandibular oral data; and a second matching operation of matching the occlusal oral data with the first facial data based on matching information of the teeth data and the oral data.

The first facial data may be acquired by scanning a facial area including the patient's nose. The first facial data may be acquired by scanning a facial area including lips and philtrum between the patient's nose and a part of teeth. The face scanning operation may scan the first facial data so that a part of the patient's teeth is included.

The matching operation may include an operation of matching second facial data including at least one of three-dimensional face scan data obtained by scanning the entire face of the patient and CT data with oral data including at least one among the maxillary oral data, the mandibular oral data, and the occlusal oral data.

The oral data including the at least one among the maxillary oral data, the mandibular oral data, and the occlusal oral data may be matched with the second facial data using the patient's nose.

An embodiment of the present disclosure provides a computer-readable recording medium in which a program for executing the method of generating the three-dimensional model for data matching is recorded.

An apparatus for generating a three-dimensional model through data matching according to an embodiment of the present disclosure includes: an oral scanner configured to acquire maxillary oral data by scanning a patient's maxillary teeth, acquire mandibular oral data by scanning mandibular teeth of the patient, acquire teeth scan data by scanning a part of the patient's teeth in a state in which the maxillary teeth and the mandibular teeth have been occluded, and acquire first facial data by scanning the patient's face; an occlusion unit configured to acquire occlusal oral data in a state in which the maxillary oral data and the mandibular oral data have been occluded using the teeth scan data; and a matching unit configured to match the first facial data with at least one among the maxillary oral data, the mandibular oral data, and the occlusal oral data.

The matching unit may include: a teeth data extraction unit configured to extract teeth data corresponding to a part of the patient's teeth from the first facial data; a first matching unit configured to match the teeth data with at least one of the maxillary oral data and the mandibular oral data; and a second matching unit configured to match the occlusal oral data with the first facial data based on matching information of the teeth data and the oral data.

The matching unit may match second facial data including at least one of three-dimensional face scan data obtained by scanning the entire face of the patient and CT data with oral data including at least one among the maxillary oral data, the mandibular oral data, and the occlusal oral data.

The matching unit may match the oral data including at least one among the maxillary oral data, the mandibular oral data, and the occlusal oral data with the second facial data using the patient's nose.

Advantageous Effects of Invention

The embodiment of the present disclosure provides the apparatus and method for generating the three-dimensional model through data matching, which provide the information that enables more accurate treatment for prosthesis manufacturing or orthodontics through multiple data matching based on the facial data, maxillary/mandibular oral data, and occlusal oral data of the patient acquired by the oral scanner, and a recording medium.

In addition, according to the embodiment of the present disclosure, it is possible to provide the integrated three-dimensional data for the entire maxillary/mandibular area of the patient such as the patient's face as well as teeth by additionally providing the information acquired by the extraoral scan together with the oral data for the patient's affected area acquired by the oral scanner.

In addition, according to the embodiment of the present disclosure, it is possible to easily check the states of the shapes of the teeth and the face before treatment and predict the expected changes after treatment during the treatment of diseases or the orthodontic treatment related to teeth and jawbone, and the three-dimensional model may be used to determine the insertion direction of the implant or design the prosthesis in consideration of the shapes of the teeth and the face around the missed affected area when planning implant surgery.

The effects of the present disclosure are not limited to the above-described effects. Other effects not mentioned may be clearly understood to those skilled in the art to which the present disclosure pertains from this specification and the accompanying drawings.

DESCRIPTION OF EMBODIMENTS

Figure 1:
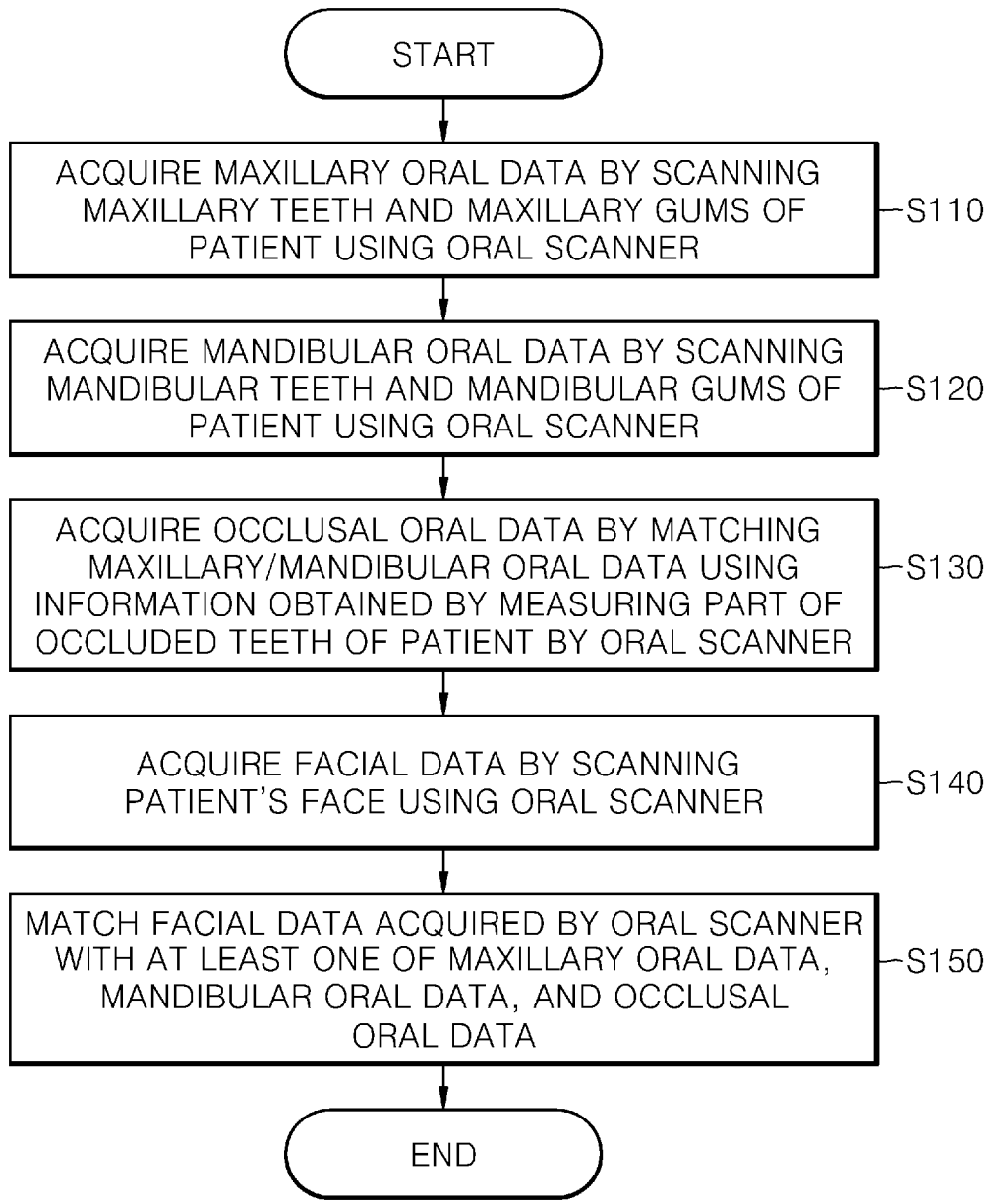
FIG. 1 is a flowchart of a method of generating a three-dimensional model through data matching according to an embodiment of the present disclosure.

Advantages and features of the present disclosure and methods of achieving them will be made clear from embodiments described in detail below with reference to the accompanying drawings. However, the present disclosure is not limited to embodiments disclosed below but will be implemented in various different forms, and only these embodiments are provided so that the disclosure of the present disclosure will be thorough and complete and will fully convey the scope of the present disclosure to those skilled in the art to which the present disclosure pertains, and the present disclosure is defined by the description of the claims.

In adding reference numerals to the components of each drawing, it should be noted that the same components are given the same reference numerals as much as possible even though they are indicated on different drawings. In addition, in describing the embodiment of the present disclosure, when it is determined that a detailed description of a related known configuration or function interferes with the understanding of the embodiment of the present disclosure, the detailed description thereof will be omitted.

In describing the components of the embodiment of the present disclosure, terms such as first and second may be used. These terms are only for distinguishing the component from another, and the essence, sequence, or order of the component is not limited by the terms. In addition, unless otherwise defined, all terms used herein, including technical or scientific terms, have the same meaning as commonly understood by those skilled in the art to which the present disclosure pertains. Terms such as those defined in a commonly used dictionary should be interpreted as having a meaning consistent with the meaning in the context of the related art, and should not be interpreted in an ideal or excessively formal meaning unless explicitly defined in this application.

In this specification, when a certain part "comprises" a certain component, it means that other components may be further included, rather than excluding other components, unless otherwise stated. As used herein, '~unit' is a unit for processing at least one function or operation, and may refer to, for example, software, FPGA, or hardware component.

In this specification, the function provided by '~unit' may be performed separately by a plurality of components, or may be integrated with other additional components. The term '~unit' in this specification is not necessarily limited to software or hardware, and may be configured to reside in an addressable storage medium, or may be configured to reproduce one or more processors. Hereinafter, embodiments of the present disclosure will be described in detail with reference to the drawings.

An apparatus and method for generating a three-dimensional model through data matching according to an embodiment of the present disclosure acquire three-dimensional maxillary oral data by scanning maxillary teeth and/or maxillary gums of a patient using an oral scanner, acquire three-dimensional mandibular oral data by scanning mandibular teeth and/or mandibular gums of the patient using the oral scanner, and then acquire three-dimensional occlusal oral data in a state in which maxillary teeth and mandibular teeth of the patient have been occluded by matching the maxillary oral data with the mandibular oral data.

The three-dimensional occlusal oral data of the patient may be generated by matching the maxillary oral data and the mandibular oral data based on scan information acquired by scanning a part of patient's teeth using the oral scanner in the state in which the maxillary teeth and the mandibular teeth of the patient have been occluded.

In one embodiment of the present disclosure, it is possible to a three-dimensional model in which facial data and oral data have been matched by designating a point of a teeth part to be matched with the oral data in the facial data of the patient, designating a point at a position corresponding to the point designated in the facial data in any one of the maxillary oral data, the mandibular oral data, and the occlusal oral data, and then performing matching between two data using an iterative closest point (ICP) method of aligning a position by minimizing a distance deviation between different two or more three-dimensional data.

In another embodiment of the present disclosure, the three-dimensional model may also be generated by acquiring three-dimensional facial data by scanning the patient's face using the oral scanner, extracting teeth data corresponding to a part of the patient's teeth from the facial data, then matching the teeth data with the maxillary oral data and/or the mandibular oral data, and matching the occlusal oral data with the facial data based on matching information of the teeth data and the three-dimensional oral data.

According to the embodiment of the present disclosure, it is possible to provide additional information that enables more accurate treatment for prosthesis manufacturing or orthodontics through multiple data matching based on the facial data, the maxillary/mandibular oral data, or the occlusal oral data acquired by the oral scanner or the like, and for example, provide integrated three-dimensional data for the entire maxillary/mandibular area and face of the patient such as the patient's face as well as teeth.

Accordingly, according to the embodiment of the present disclosure, it is possible to easily check the states of shapes of teeth and the face before treatment and easily predict expected changes after treatment during the treatment of diseases and orthodontic treatment related to teeth and jawbone by matching information acquired by an extraoral scan with the oral data and additionally providing the matched information together with the oral data for the patient's affected area acquired by the oral scanner.

The method of generating the three-dimensional model through data matching according to the embodiment of the present disclosure may be used for various dental treatments such as determining an insertion direction of an implant or designing a prosthesis in consideration of shapes of teeth and a face around a missed affected area of the patient when planning implant surgery.

FIG. 1 is a flowchart of a method of generating a three-dimensional model through data matching according to an embodiment of the present disclosure. Referring to FIG. 1, the method for generating the three-dimensional model through data matching according to the embodiment of the present disclosure includes a maxilla scanning operation (S110), a mandible scanning operation (S120), an occluding operation (S130), a face scanning operation (S140), and a matching operation (S150).

First, a dental professional may acquire maxillary oral data by scanning a patient's maxillary teeth and maxillary gums (scanning an inside of an oral cavity), and acquire mandibular oral data by scanning the patient's mandibular teeth and mandibular gums using an oral scanner (S110 and S120).

As an oral scanner 110, for example, a scanner such as a triangulation-based optical scanner or a confocal laser microscope-based scanner may be used, but the present disclosure is not limited thereto. The oral scanner 110 may project structured light to an object to be measured by a light source, acquire a two-dimensional image through a camera, and then implement the two-dimensional image as a three-dimensional virtual model, which may be recorded in the form of a polygon mesh.

By acquiring maxillary oral data and mandibular oral data, and then matching the maxillary/mandibular oral data using information obtained by measuring a part of the patient's occluded teeth by the oral scanner 110, an occluding operation of acquiring three-dimensional occlusal oral data in a state in which the patient's maxillary teeth and mandibular teeth have been occluded may be performed (S130).

In the embodiment of the present disclosure, in the occluding operation (S130), occlusal teeth scan information may be acquired by measuring both side portions (e.g., molar portions) of the patient's teeth using the oral scanner 110 in the state in which the patient's maxillary teeth and mandibular teeth have been occluded, and occlusal oral data may be acquired by matching the maxillary oral data with the mandibular oral data based on the occlusal teeth scan information.

In addition, facial data (first facial data) may be acquired by scanning the patient's face (extraoral scan) using the oral scanner 110 (S140). The facial data may be acquired by scanning a facial area for a part of a front portion of the oral cavity including the lips, philtrum, nose, and a part of teeth of the patient.

The oral scanner 110 may generate three-dimensional surface data having a relatively high accuracy (e.g., about 20 um or less). Accordingly, sophisticated three-dimensional maxillary oral data, three-dimensional mandibular oral data, and three-dimensional facial data may be acquired by the oral scanner 110.

In one embodiment of the present disclosure, a three-dimensional model in which the facial data and the oral data have been matched may be generated by designating a point of a teeth part to be matched with the oral data in the patient's facial data, designating a point at a position corresponding to the point designated in the facial data in any one of the maxillary oral data, the mandibular oral data, and the occlusal oral data, and then performing matching between two data using an iterative closest point (ICP) method.

When the three-dimensional facial data of the patient is generated by the oral scanner 110, the facial data may be matched with the oral data of at least one of the maxillary oral data, the mandibular oral data, and the occlusal oral data (S150). At this time, the three-dimensional model in which the facial data and the oral data have been matched may be generated by designating the point of the teeth part to be matched with the oral data in the facial data of the patient, designating the point at the position corresponding to the point designated in the facial data in the oral data, and then performing matching between two data using the iterative closest point (ICP) method.

Figure 2:
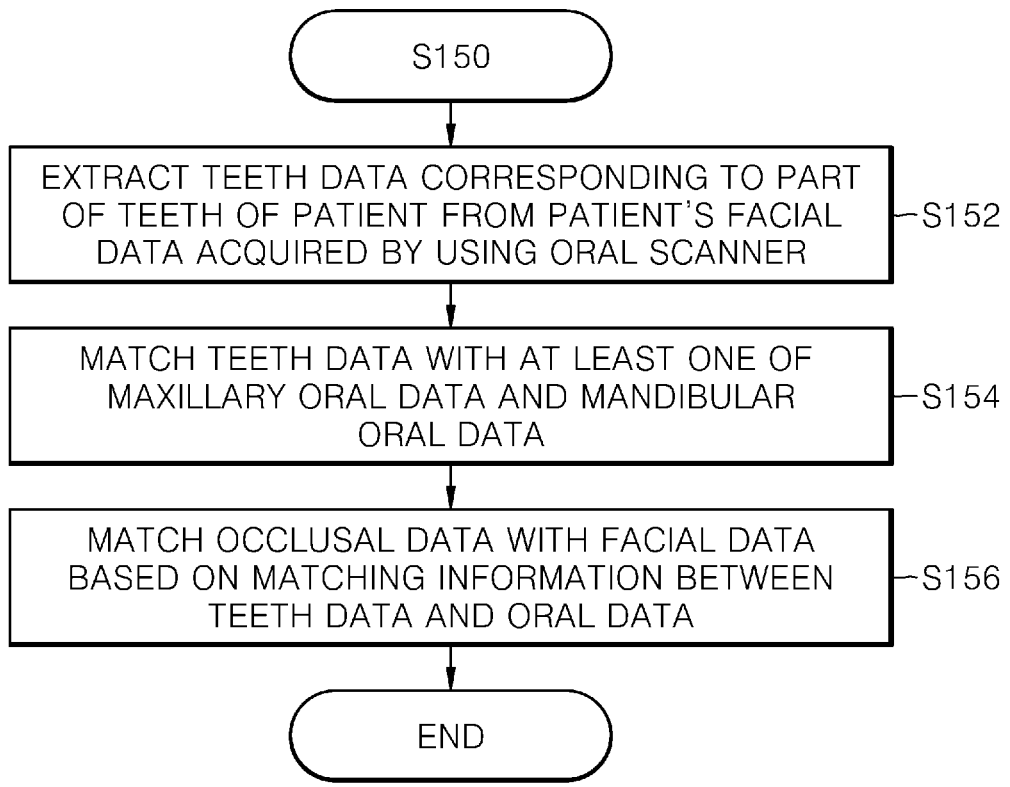
FIG. 2 is a flowchart of operation S150 in FIG. 1.

Alternatively, the facial data and the oral data may also be matched by extracting the teeth data from the facial data and then matching the teeth data with the oral data. FIG. 2 is a flowchart of operation S150 in FIG. 1. Referring to FIG. 2, teeth data corresponding to a part of the patient's teeth (a part of the maxillary teeth and/or a part of the mandibular teeth) may be extracted from the patient's facial data (S152). At this time, the teeth data may be extracted based on the shape information and color information of the teeth.

When the teeth data corresponding to a part of the teeth is extracted from the three-dimensional facial data of the patient, at least one three-dimensional oral data of the maxillary oral data and mandibular oral data of the patient is matched with the teeth data extracted from the three-dimensional facial data (S154). The maxillary/mandibular oral data and the teeth data may be matched, for example, by an iterative closest point (ICP) algorithm.

By the ICP algorithm, vertices may be extracted (sampled) on surfaces of the maxillary/mandibular oral data, and a corresponding point corresponding to each vertex may be extracted from the teeth data, and then an objective function corresponding to energies of distance values for a vertex-corresponding point group may be calculated.

At this time, the vertex does not necessarily mean a point that satisfies a specific condition on the surface data, and all points on the surface of the surface data may be a vertex. A method of extracting vertices from the surface data is not limited to a particular method, and the vertices may be extracted by various methods known in the field of data processing.

One or a plurality of vertices may be extracted from the surface data, and as the number of extracted vertices increases, the matching accuracy may be improved. When one or more pairs of extracted vertices and their corresponding points are secured, the objective function may be calculated therefrom, and a movement function between the maxillary/mandibular oral data and the teeth data that minimizes a value of the objective function (three-dimensional movement transformation matrix or 3-axis rotation transformation matrix) may be calculated.

In addition, by repeatedly performing a process of moving the position of the maxillary/mandibular oral data or the teeth data by the movement function between the maxillary/mandibular oral data and the teeth data until a predetermined end condition is satisfied, it is possible to match the maxillary/mandibular oral data and the teeth data.

When the three-dimensional teeth data and the three-dimensional oral data are completely matched, the three-dimensional facial data may be matched with the three-dimensional occlusal oral data (data scanned by the oral scanner in the state in which the maxillary teeth and the mandibular teeth have been occluded or data in which the three-dimensional maxillary oral data and the three-dimensional mandibular oral data scanned by the oral scanner have been matched in the state of being occluded) based on the matching information of the teeth data and the oral data (S156).

In the embodiment of FIG. 2, after the teeth data extracted from the facial data is matched with the maxillary or mandibular oral data, the facial data is matched with the occlusal oral data based on the matching information of the teeth data and the maxillary or mandibular oral data, but the occlusal oral data may also be directly matched with the teeth part of the facial data by the ICP method or the like by designating points on the teeth part of the facial data and the teeth part of the occlusal oral data, respectively.

In addition, in the embodiment of FIGS. 1 and 2, the three-dimensional model may be generated by matching the facial data (the first facial data) acquired by the oral scanner with the oral data (the maxillary oral data, the mandibular oral data, or the occlusal oral data), but the CT data or the three-dimensional facial scan data (the second facial data) obtained by scanning the entire face may also be matched with the oral data.

Figure 3:
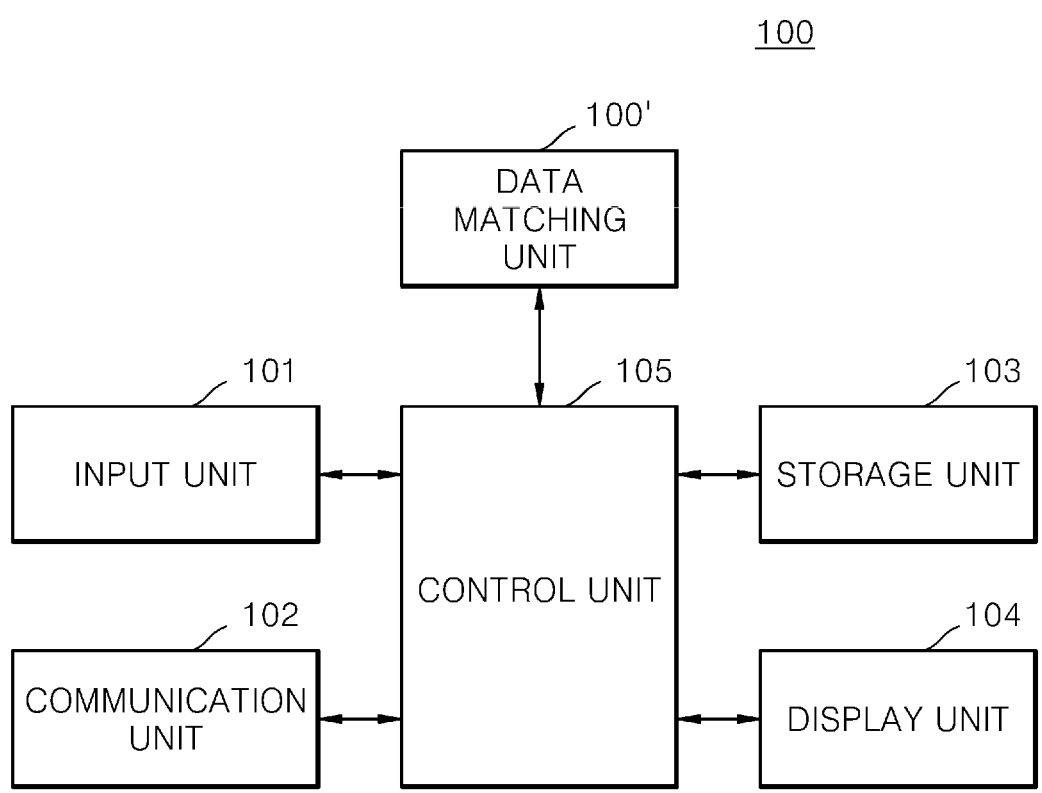
FIG. 3 is a block view of an apparatus for generating a three-dimensional model through data matching according to an embodiment of the present disclosure.
Figure 4:
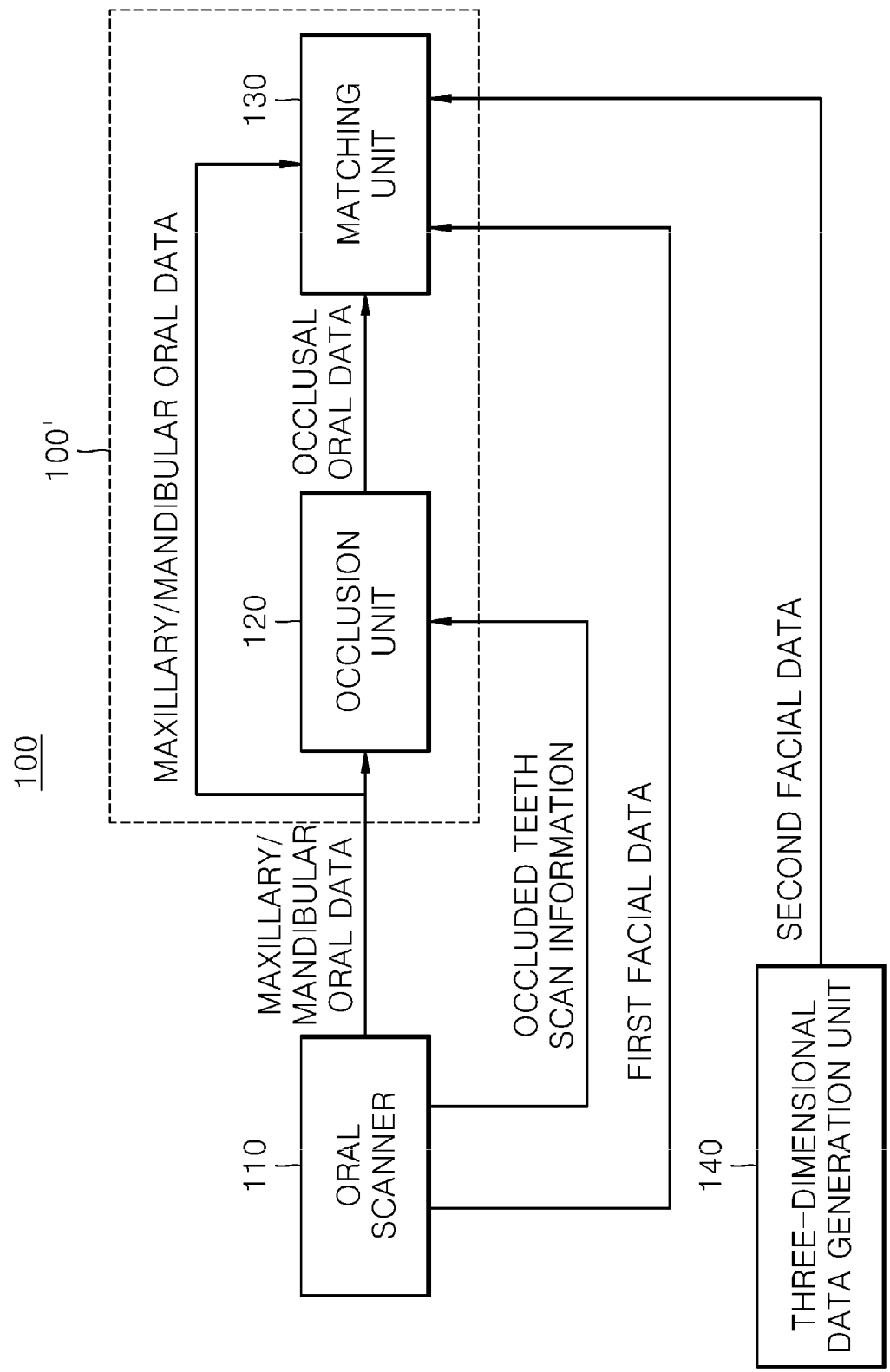
FIG. 4 is a block view of a data matching unit configuring the apparatus for generating the three-dimensional model through data matching according to the embodiment of the present disclosure.

FIG. 3 is a block view of an apparatus for generating a three-dimensional model through data matching according to an embodiment of the present disclosure. FIG. 4 is a block view of a data matching unit configuring the apparatus for generating the three-dimensional model through data matching according to the embodiment of the present disclosure. Referring to FIGS. 1 to 4, an apparatus 100 for generating a three-dimensional model through data matching according to an embodiment of the present disclosure includes an input unit 101, a communication unit 102, a storage unit 103, a display unit 104, a control unit 105, a data matching unit 100', the oral scanner 110, and a three-dimensional data generation unit 140.

The apparatus 100 for generating the three-dimensional model through data matching according to the embodiment of the present disclosure may be provided to, for example, a medical terminal for dental treatment. The medical terminal may be implemented as, for example, a desktop PC, a tablet PC, a laptop PC, a netbook computer, a smart phone, a workstation, a PDA, a PMP, or a wearable device, but is not limited thereto.

The input unit 101 may include a user interface configured to receive various commands such as generation of the three-dimensional model from a user such as a medical professional. The input unit 101 may be provided as a keyboard, a mouse, a touch pad, at least one button or switch, an input means through recognition of a user's gesture, or a user interface configured to perform a function equivalent thereto.

The input unit 101 may be provided to input various commands such as reading the maxillary oral data, mandibular oral data, occlusal oral data, facial data, and the like of the patient from the storage unit 103, generating the occlusal oral data by matching the maxillary oral data with the mandibular oral data, matching one or more of the maxillary oral data, the mandibular oral data, and the occlusal oral data with the facial data, or matching the maxillary/mandibular oral data with the teeth data extracted from the facial data by the medical professional.

The communication unit 102 may provide a wired/wireless communication interface configured to receive data acquired by the oral scanner 110. A communication interface may include local area network (LAN), integrated services digital network (ISDN), code division multiple access (CDMA), wideband code division multiple access (WCDMA), global system for mobile communication (GSM), long term evolution (LTE), world interoperability for microwave access (WIMAX), wireless local area network (LAN), wide area network (WAN), wireless fidelity (WIFI), or the like, but is not limited thereto.

The storage unit 103 may store a program for generating the three-dimensional model through data matching, and other various types of information. The storage unit 103 may store the maxillary/mandibular oral data of the patient, occlusal oral data in the state in which the maxillary teeth and the mandibular teeth have been occluded, facial data, data in which the facial data has been matched with the oral data (the maxillary oral data, the mandibular oral data, or the occlusal oral data), and the like.

The storage unit 103 may be a storage medium such as a volatile memory such as static RAM (SRAM), or dynamic RAM (DRAM), synchronous DRAM (SDRAM), a non-volatile memory such as read only memory (ROM), programmable ROM (PROM), electrically programmable ROM (EPROM), or electrically erasable and programmable ROM (EEPROM), flash memory, phase-change RAM (PRAM), magnetic RAM (MRAM), resistive RAM (RRAM), ferroelectric RAM (FRAM), an optical media such as floppy disk, hard disk, or optically readable medium, for example, such as CD-ROM or DVD, or a magnetic media such as a magnetic tape, but is not limited thereto.

The display unit 104 may display information such as a three-dimensional virtual model (e.g., the maxillary/mandibular oral data, occlusal oral data, facial data, and data in which the facial data has been matched with the oral data of the patient) on a display screen. The display unit 104 may be provided as a display device such as a liquid crystal display (LCD) or a light emitting diode (LED) display, but is not limited thereto.

The control unit 105 may control functions and operations of the respective components of the apparatus for generating the three-dimensional model by applying various control commands for generating the three-dimensional model through data matching, and execute a function such as executing a program for generating the three-dimensional model including the oral cavity and face of the patient. The control unit 105 may include one or more processors.

The control unit 105 may execute a program for controlling the data matching unit 100' to match the maxillary/mandibular oral data acquired by the oral scanner 110 or the occlusal oral data in which the maxillary/mandibular oral data have been matched with the facial data, or match the maxillary oral data and the mandibular oral data in the state of being occluded.

Figure 5:
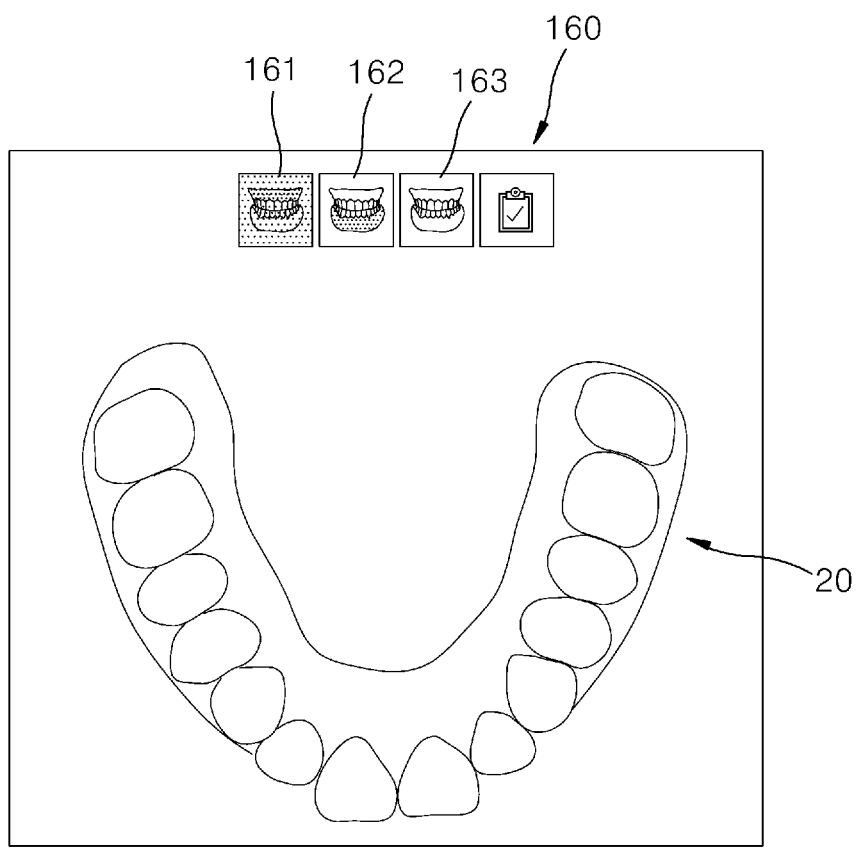
FIG. 5 is an exemplary view of maxillary oral data generated by an oral scanner configuring the apparatus for generating the three-dimensional model through data matching according to the embodiment of the present disclosure.
Figure 6:
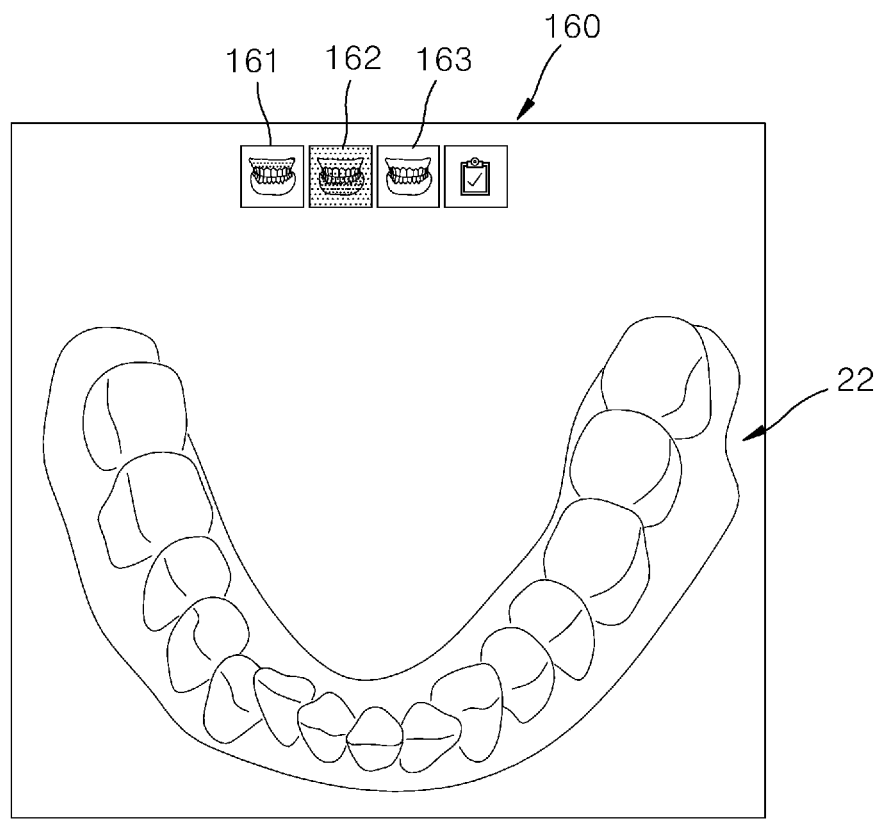
FIG. 6 is an exemplary view of mandibular oral data generated by the oral scanner configuring the apparatus for generating the three-dimensional model through data matching according to the embodiment of the present disclosure.

The data matching unit 100' generates the three-dimensional virtual model in which the oral data and the facial data are integrated by matching the three-dimensional oral data acquired by the oral scanner 110 and the three-dimensional facial data, and may include an occlusion unit 120 and a matching unit 130. FIG. 5 is an exemplary view of maxillary oral data generated by an oral scanner configuring the apparatus for generating the three-dimensional model through data matching according to the embodiment of the present disclosure. FIG. 6 is an exemplary view of mandibular oral data generated by the oral scanner configuring the apparatus for generating the three-dimensional model through data matching according to the embodiment of the present disclosure.

Referring to FIGS. 1, and 4 to 6, the oral scanner 110 may acquire maxillary oral data 20 by scanning the maxillary teeth and/or the maxillary gums of the patient, and acquire mandibular oral data 22 by scanning the mandibular teeth and/or the mandibular gums of the patient (S110 and S120).

As the oral scanner 110, for example, a scanner such as a triangulation-based optical scanner or a confocal laser microscope-based scanner may be used. The oral scanner 110 may project structured light to an object to be measured by a light source, acquire a two-dimensional image through a camera, and then implement the two-dimensional image as a three-dimensional virtual model, which may be recorded in the form of a polygon mesh.

Figure 7:
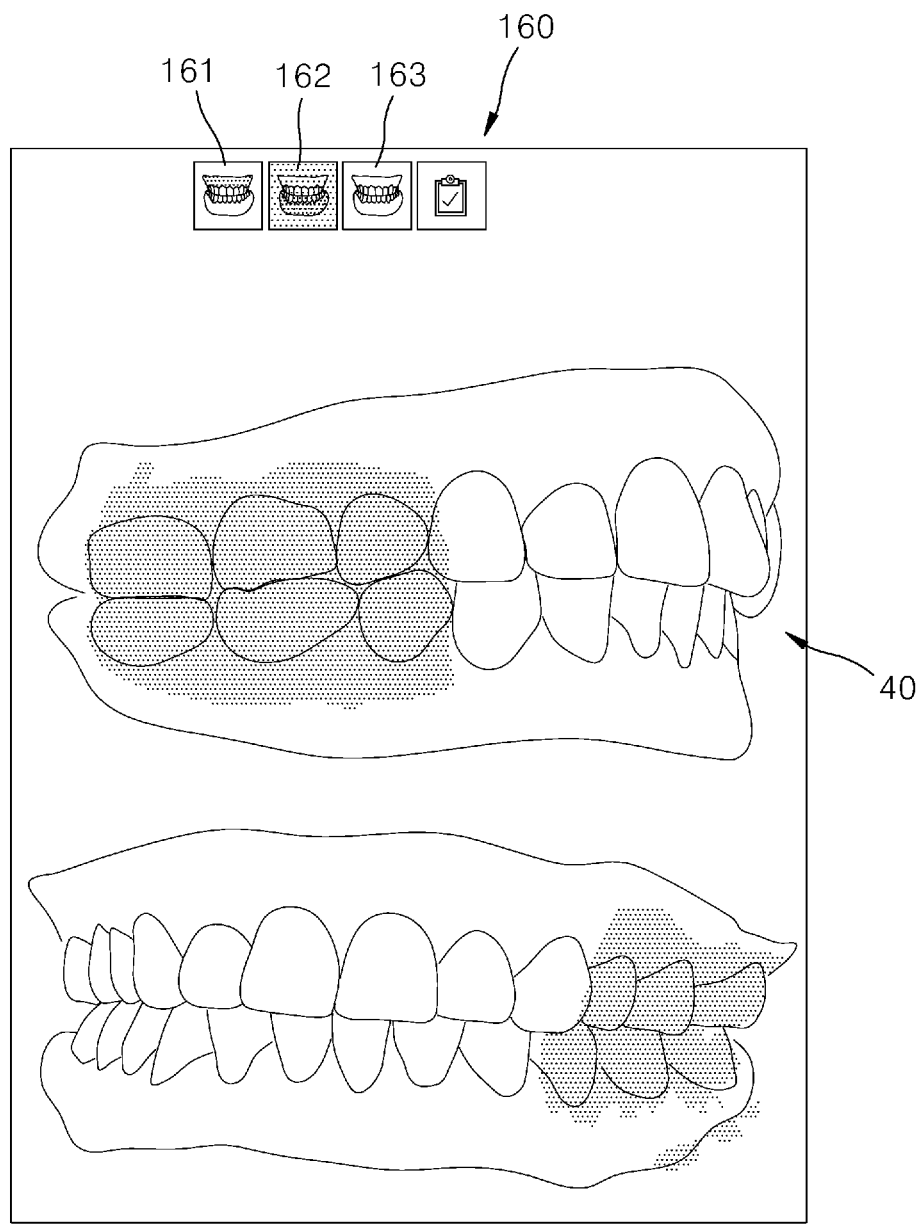
FIG. 7 is an exemplary view of occlusal oral data generated by an occlusion unit configuring the apparatus for generating the three-dimensional model through data matching according to the embodiment of the present disclosure.

FIG. 7 is an exemplary view of an occlusal oral data generated by an occlusion unit configuring the apparatus for generating the three-dimensional model through data matching according to the embodiment of the present disclosure. Referring to FIGS. 1, 4, and 7, the occlusion unit 120 may acquire occlusal oral data 40 in the state in which the maxillary teeth and the mandibular teeth have been occluded, as shown in FIG. 7, based on the data scanned by the oral scanner 110 (S130).

A portion measured for the occluded teeth through the oral scanner 110 is shown in a predetermined color or pattern in FIG. 7. When the teeth of the predetermined number of maxillas and mandibles (6 in the example of FIG. 7) are scanned at the side portion (e.g., the molar portion) of the teeth, the maxillary oral data and the mandibular oral data may be matched in a state of being occluded based on the corresponding scan data. When the teeth data is measured at only one side of the teeth, the maxillary/mandibular oral data may not fit at the opposite side (opposite molar portion), so that it is possible to acquire the occlusal oral data from measurement information (teeth scan information) of both side portions of the teeth in the occluded state by also measuring the opposite side portion of the teeth.

The matching unit 130 may generate the three-dimensional model in which the first facial data and the oral data have been matched by matching the first facial data and the oral data using the iterative closest point (ICP) method based on one or more points designated on the teeth part to be matched with the oral data among the first facial data of the patient acquired by the oral scanner 110, and one or more points designated at a position corresponding to the point designated in the first facial data among the oral data. In addition, the matching unit 130 may generate the three-dimensional model in which the second facial data and the oral data have been matched by matching the CT data generated by the three-dimensional data generation unit 140 or the three-dimensional facial scan data (second facial data) obtained by scanning the entire face with the oral data.

A maxilla scan object 161 configured to scan the maxillary oral data, a mandible scan object 162 configured to scan the mandibular oral data, and an occlusal object 163 configured to acquire the occlusal oral data matched by occluding the maxillary/mandibular oral data by the medical professional may be displayed on a user interface screen 160, and the oral data may be acquired by selecting the corresponding objects 161, 162, and 163.

Figure 8:
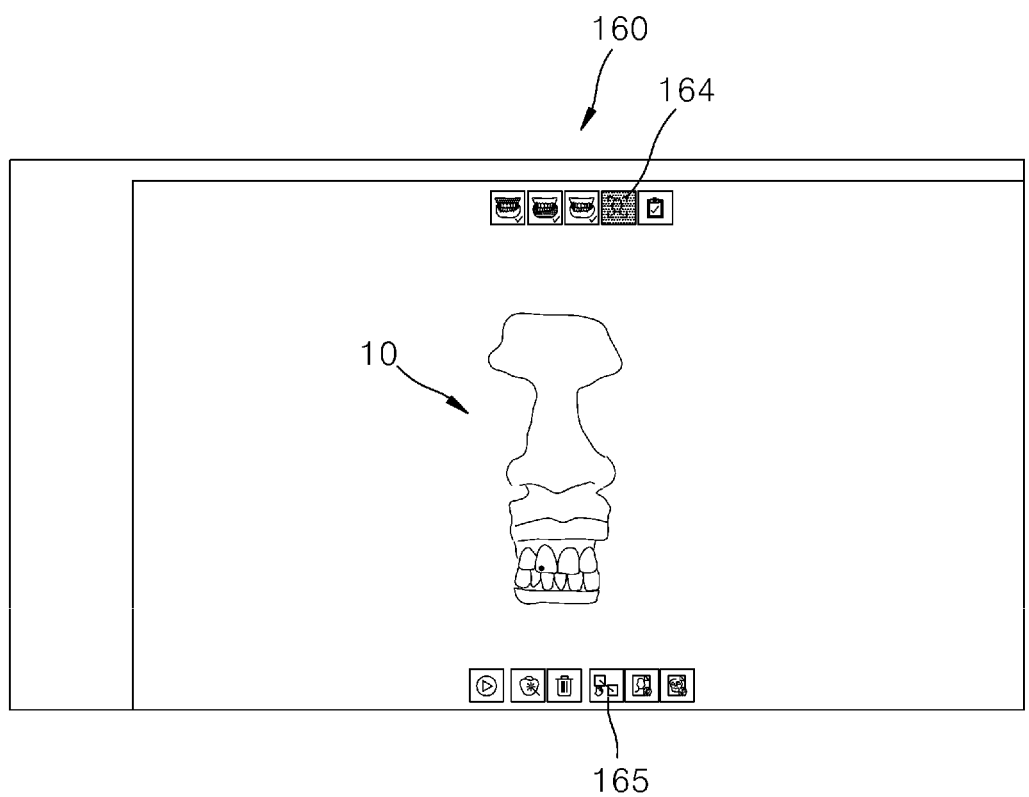
FIG. 8 is an exemplary view of facial data generated by the oral scanner configuring the apparatus for generating the three-dimensional model through data matching according to the embodiment of the present disclosure.

FIG. 8 is an exemplary view of facial data generated by the oral scanner configuring the apparatus for generating the three-dimensional model through data matching according to the embodiment of the present disclosure. Referring to FIGS. 1, 4, and 8, the oral scanner 110 may acquire facial data 10 of the patient by scanning a facial area including the lips, philtrum, nose, and a part of teeth of the patient (S140).

An object 164 configured to input commands displayed on the screen by scanning the facial data 10 by the medical professional may be displayed on the user interface screen 160. The facial data 10 scanned by the oral scanner 110 may be displayed on the user interface screen 160 of the medical terminal.

Figure 9:
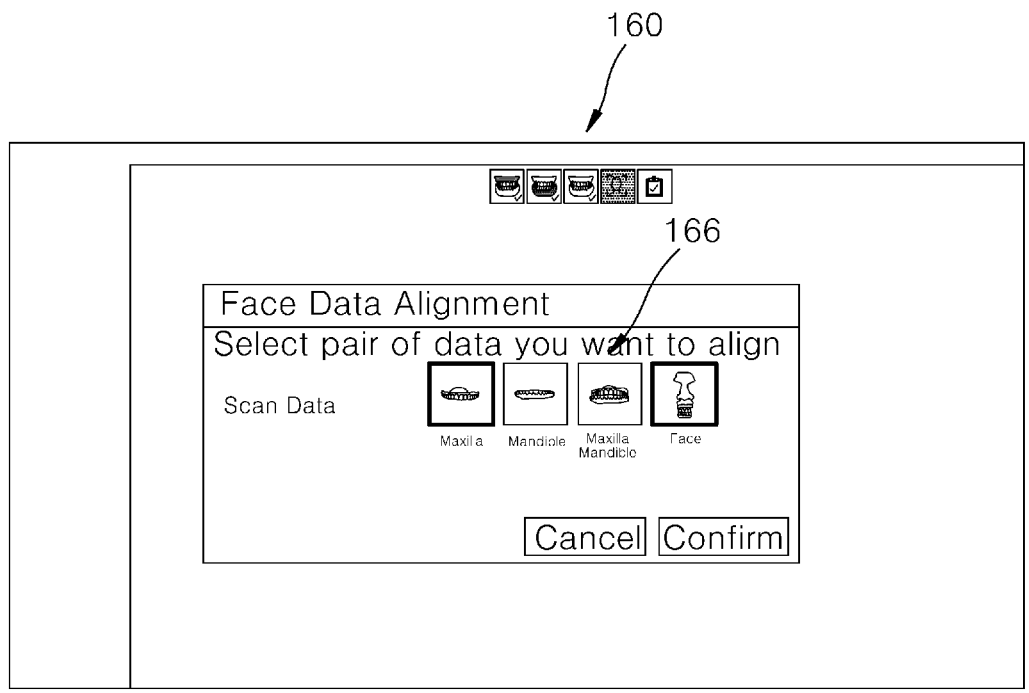
FIG. 9 is an exemplary view showing a screen on which oral data to be matched with the facial data is selected according to the embodiment of the present disclosure.

FIG. 9 is an exemplary view showing a screen on which oral data to be matched with the facial data is selected according to the embodiment of the present disclosure. A matching object 165 configured to input commands for executing the matching functions of the facial data 10 and the oral data 20, 22, and 40 by the medical professional may be displayed on the user interface screen 160. When the medical professional inputs the matching object 165 configured to execute the matching function of the facial data and the oral data on the user interface screen 160, a selection object 166 capable of selecting the oral data (the maxillary oral data, the mandibular oral data, or the occlusal oral data) to be matched with the facial data may be displayed.

Figure 10:
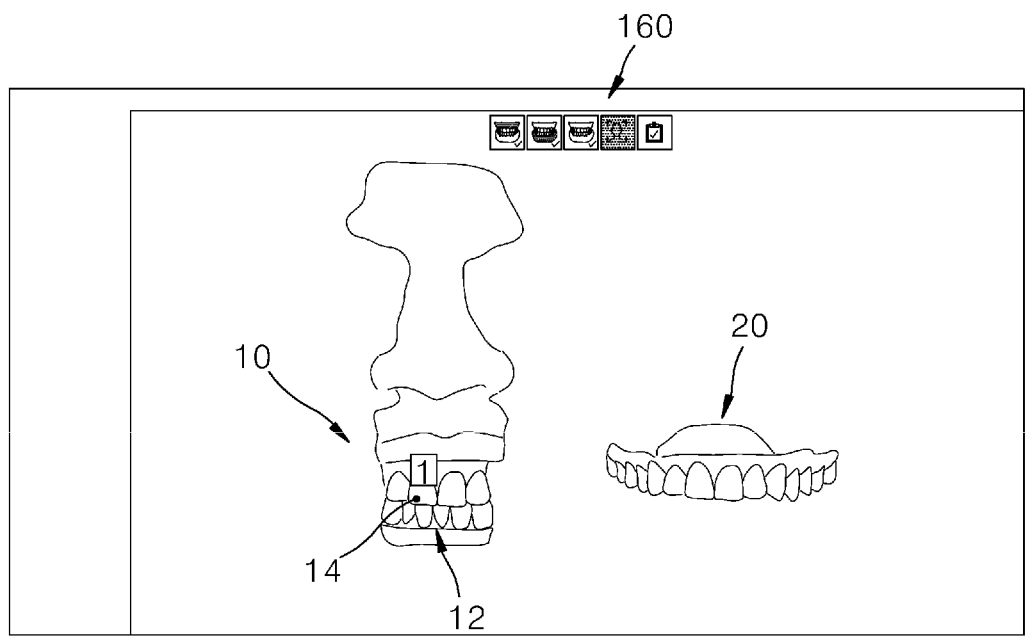
FIG. 10 is an exemplary view showing a screen on which the oral data to be matched with the facial data has been selected according to the embodiment of the present disclosure.
Figure 11:
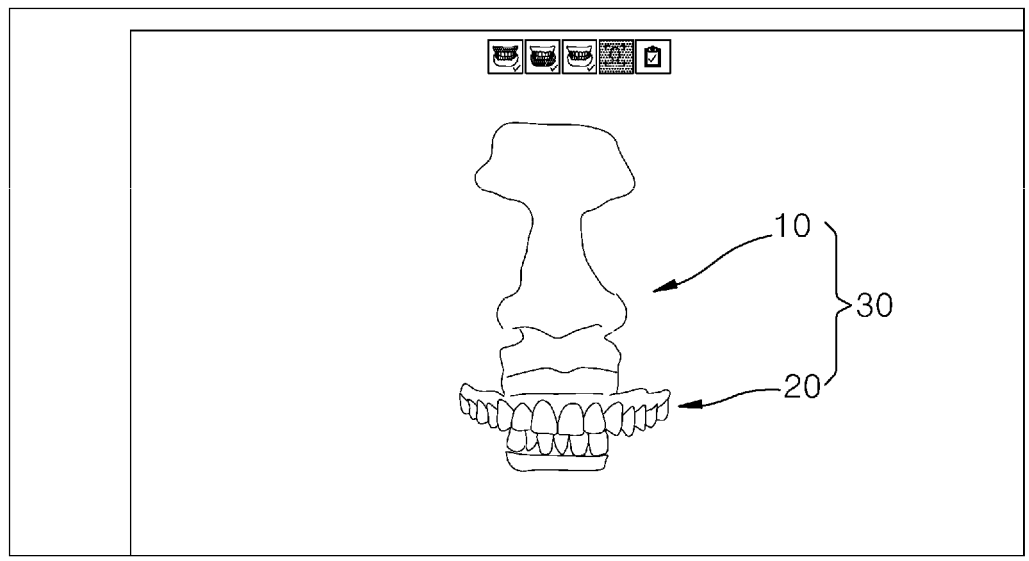
FIG. 11 is a view showing that the facial data and maxillary oral data have been matched according to the embodiment of the present disclosure.
Figure 12:
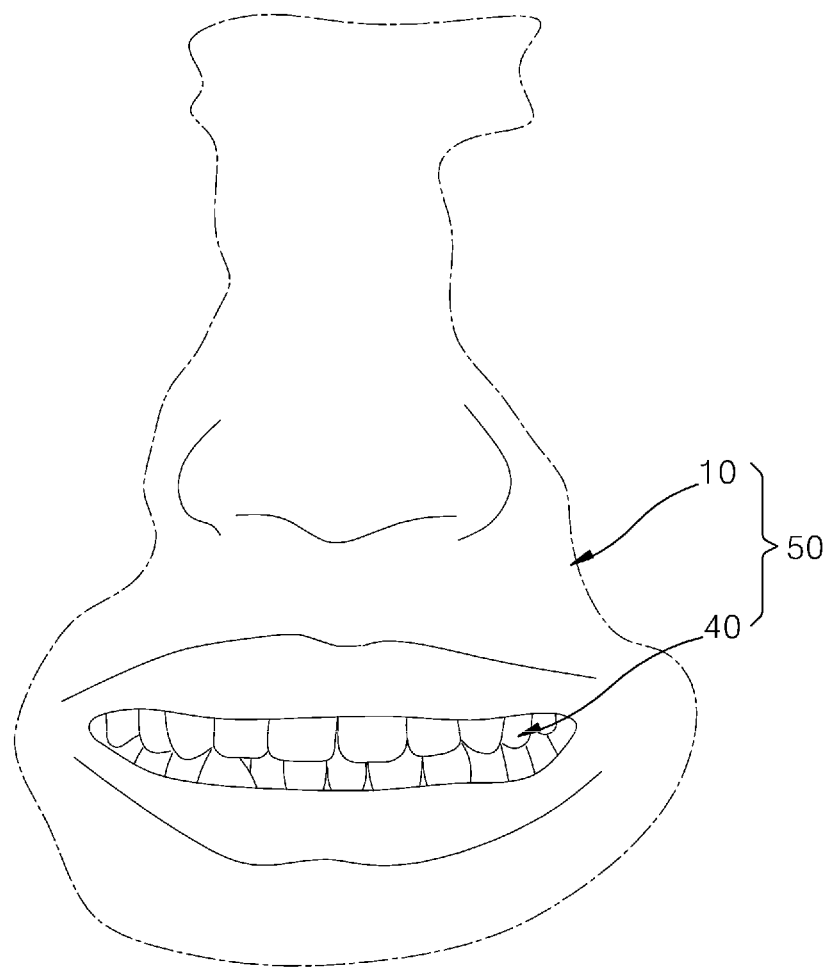
FIGS. 12 to 14 are views showing that the facial data and the oral data have been matched according to the embodiment of the present disclosure.
Figure 13:
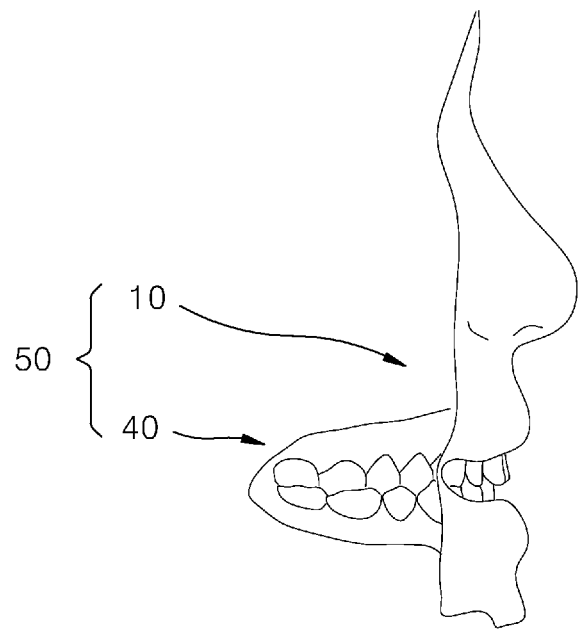
Figure 14:
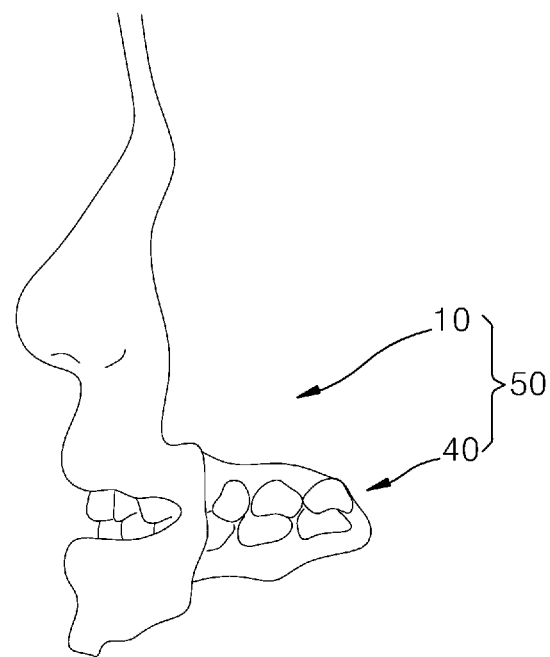

FIG. 10 is an exemplary view showing a screen on which the oral data to be matched with the facial data has been selected according to the embodiment of the present disclosure. FIG. 11 is a view showing that the facial data and maxillary oral data have been matched according to the embodiment of the present disclosure. FIGS. 12 to 14 are views showing that the facial data and the oral data have been matched according to the embodiment of the present disclosure.

Referring to FIGS. 1, 4, and 9 to 14, when one or more points 14 are designated in a teeth part 12 of the patient of the first facial data 10 of the patient acquired by using the oral scanner 110 and a point corresponding to the point 14 designated in the first facial data 10 is designated in the oral data (the maxillary oral data, the mandibular oral data, or the occlusal oral data), the matching unit 130 may generate three-dimensional models 30 and 50 in which the first facial data 10 and the oral data 20 and 40 have been matched by matching the first facial data 10 and the oral data 20 and 40.

The oral data 20 and 40 and the first facial data 10 may be matched by, for example, the iterative closest point (ICP) algorithm. By the ICP algorithm, it is possible to calculate an objective function corresponding to the distance energies of a pair of corresponding points between the points designated in the oral data 20 and 40 and the point designated in the first facial data 10.

The oral data 20 and 40 and the first facial data may be matched by calculating the movement function between the oral data 20 and 40 and the first facial data 10 to minimize the value of the objective function, and repeatedly performing the process of moving the position of the oral data 20 and 40 or the first facial data 10 by the movement function until the end condition is satisfied.

According to the embodiment of the present disclosure, it is possible to provide the three-dimensional model in which the oral data and the facial data have been integrated that enables more accurate treatment for prosthesis manufacturing or orthodontics by matching a part of the teeth part acquired by measuring the face scan by an extraoral scan with the oral data acquired by an intraoral scan corresponding thereto.

In other words, according to the embodiment of the present disclosure, it is possible to provide the integrated three-dimensional data for the entire maxillary/mandibular area of the patient such as the patient's face as well as teeth by additionally providing information acquired by the extraoral scan together with the oral data for the patient's affected area acquired by the oral scanner.

Accordingly, there are advantages in that it is possible to easily check the states of the shapes of the teeth and the face before treatment during the treatment of diseases and the orthodontic treatment related to teeth and jawbone and easily predict the expected changes after treatment, and the three-dimensional model may be used to determine the insertion direction of the implant or design the prosthesis in consideration of the shapes of the teeth and the face around the missed affected area when planning implant surgery.

Figure 15:
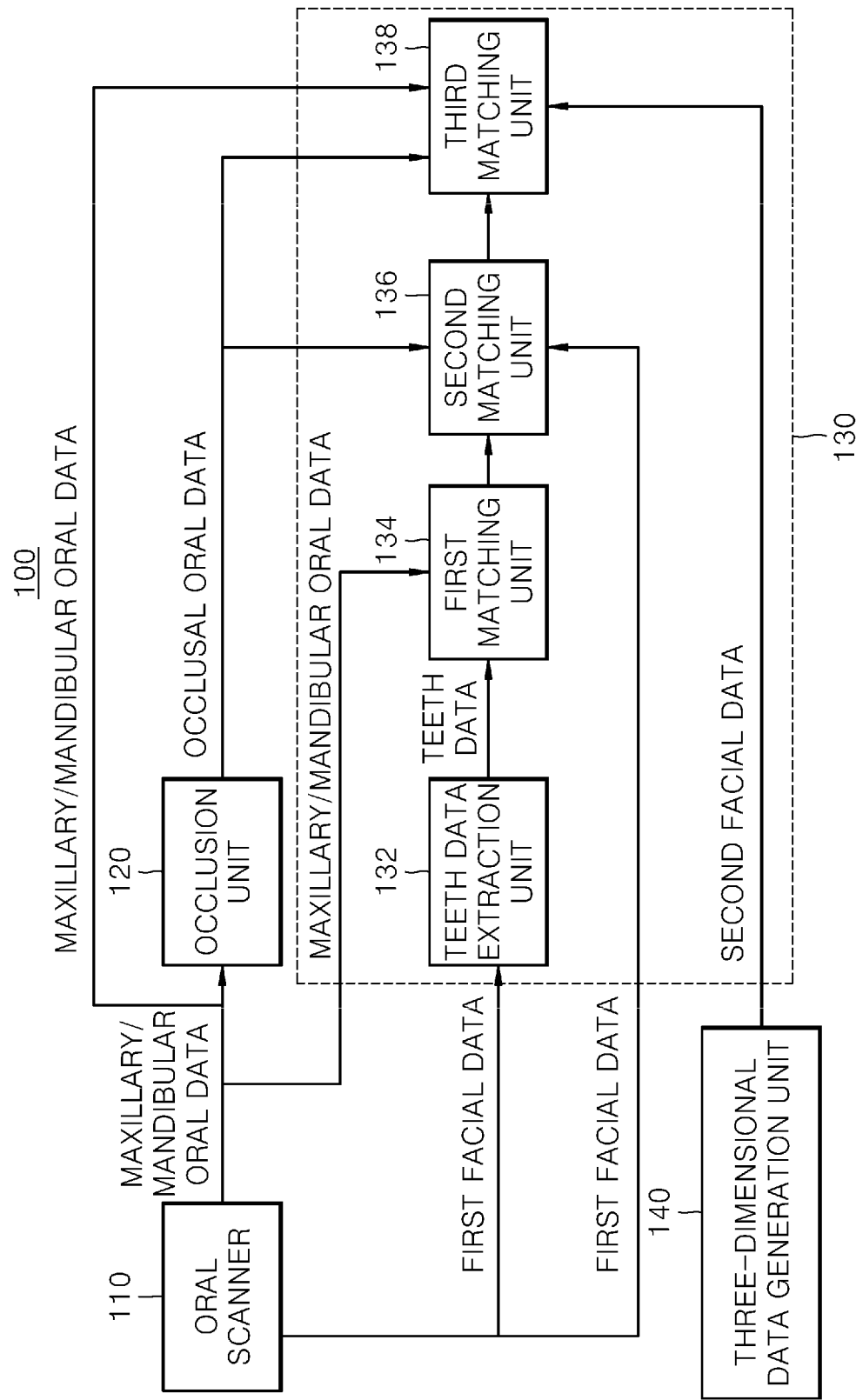
FIG. 15 is a block view of an apparatus for generating a three-dimensional model through data matching according to another embodiment of the present disclosure.

FIG. 15 is a block view of an apparatus for generating a three-dimensional model through data matching according to another embodiment of the present disclosure. Referring to FIG. 15, the matching unit 130 may include a teeth data extraction unit 132, a first matching unit 134, a second matching unit 136, and a third matching unit 138. The teeth data extraction unit 132 may extract teeth data corresponding to a part of the patient's teeth from the patient's first facial data acquired by using the oral scanner 110.

The first matching unit 134 may generate the three-dimensional model 30 in which the first facial data and the maxillary/mandibular oral data have been matched by matching the teeth data 12 extracted by the teeth data extraction unit 132 with the maxillary oral data and/or the mandibular oral data to match the first facial data 10 with the maxillary/mandibular oral data.

The second matching unit 136 may generate the three-dimensional model in which the facial data and the occlusal oral data have been matched by matching the occlusal oral data with the first facial data based on the matching information of the teeth data extracted by the teeth data extraction unit 132 and the maxillary/mandibular oral data.

The third matching unit 138 may generate the three-dimensional model in which the second facial data and the oral data have been matched by matching the CT data generated by the three-dimensional data generation unit 140 or the three-dimensional facial scan data (the second facial data) obtained by scanning the entire face with the oral data (the data including the maxillary oral data, the mandibular oral data, or the occlusal oral data). In the embodiment, the third matching unit 138 may match the oral data with the second facial data using the patient's nose.

Figure 16:
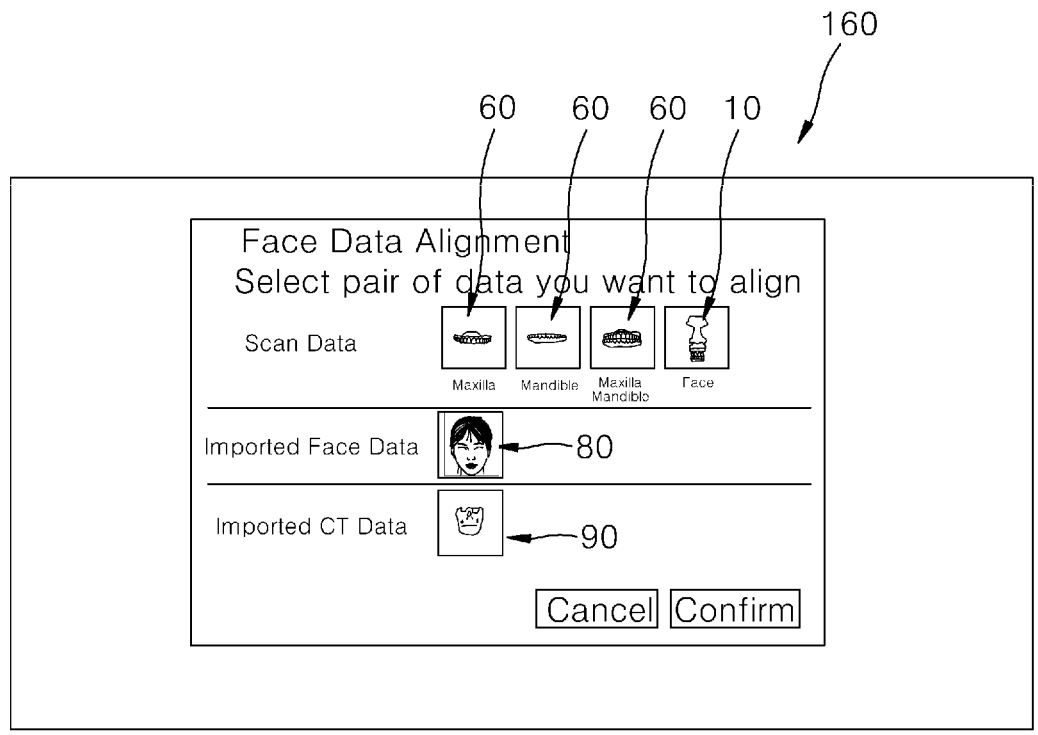
FIG. 16 is an exemplary view showing a screen on which facial data and oral data to be matched may be selected according to the embodiment of the present disclosure.

FIG. 16 is an exemplary view showing a screen on which facial data and oral data to be matched may be selected according to the embodiment of the present disclosure. On the display screen, the medical professional may select the second facial data of any one of three-dimensional face scan data 80 obtained by scanning the entire face and CT data 90, and select any one oral data 60 among the maxillary oral data, the mandibular oral data, the occlusal oral data, or the facial data 10 in which the oral data has been matched.

Figure 17:
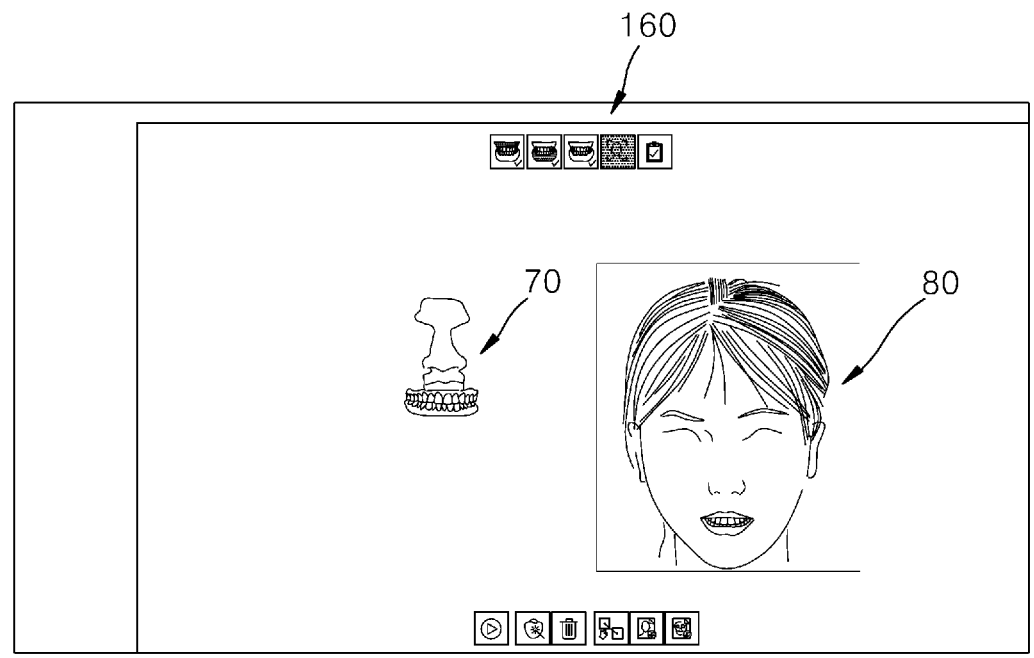
FIG. 17 is an exemplary view showing a screen on which oral data in which occlusal oral data and first facial data have been matched, and three-dimensional face scan data have been selected according to the embodiment of the present disclosure.

FIG. 17 is an exemplary view showing a screen on which oral data in which occlusal oral data and first facial data have been matched, and three-dimensional face scan data have been selected according to the embodiment of the present disclosure. FIGS. 18 to 21 are exemplary views for describing a process of matching oral data with second facial data according to the embodiment of the present disclosure. The embodiment of FIGS. 17 to 21 shows an example in which the three-dimensional face scan data 80 is selected as the second facial data, and data 70 in which the occlusal oral data and the first facial data have been matched is selected as the oral data.

Figure 18:
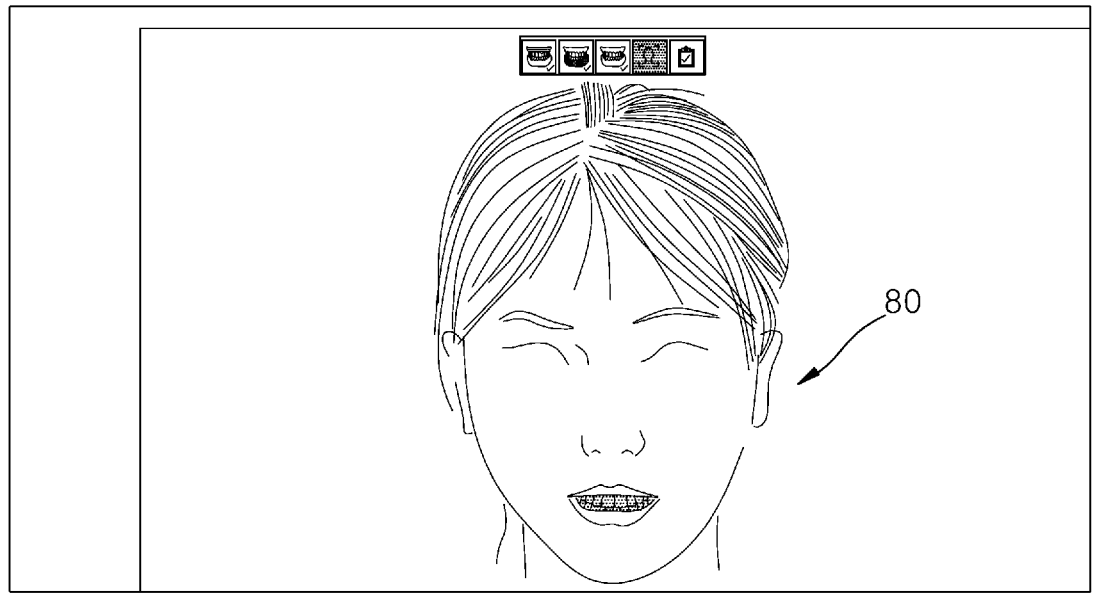
FIGS. 18 to 21 are exemplary views for describing a process of matching oral data with second facial data according to the embodiment of the present disclosure.
Figure 19:
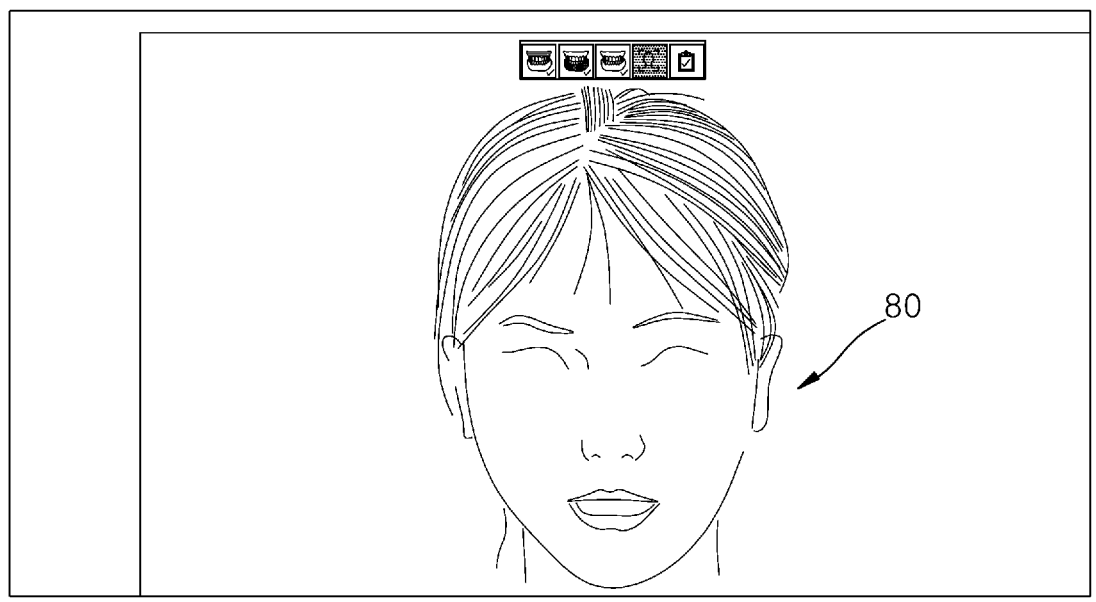
Figure 20:
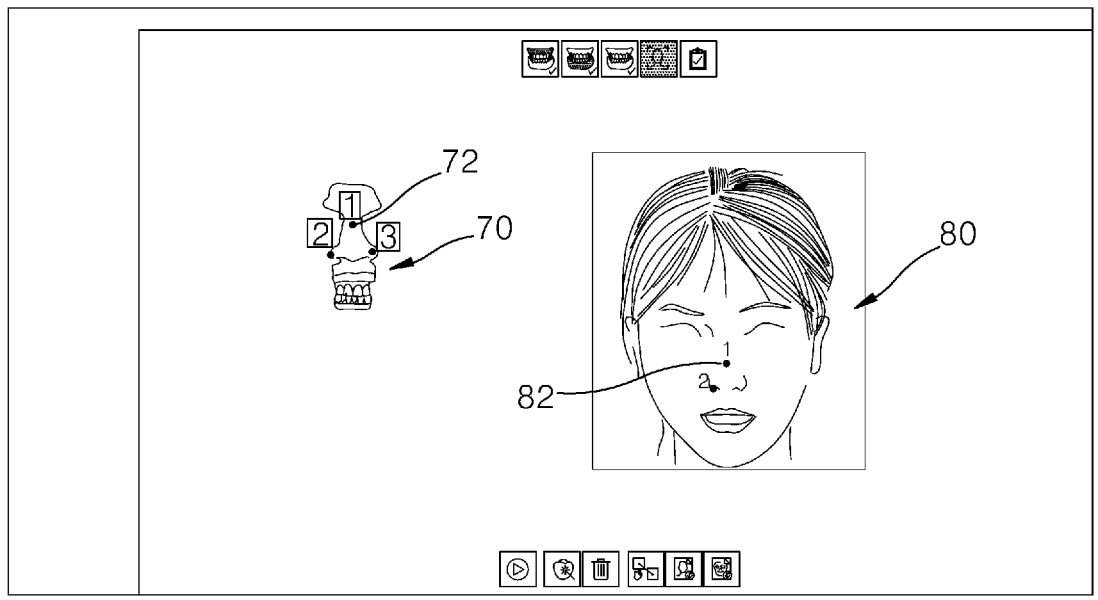
Figure 21:
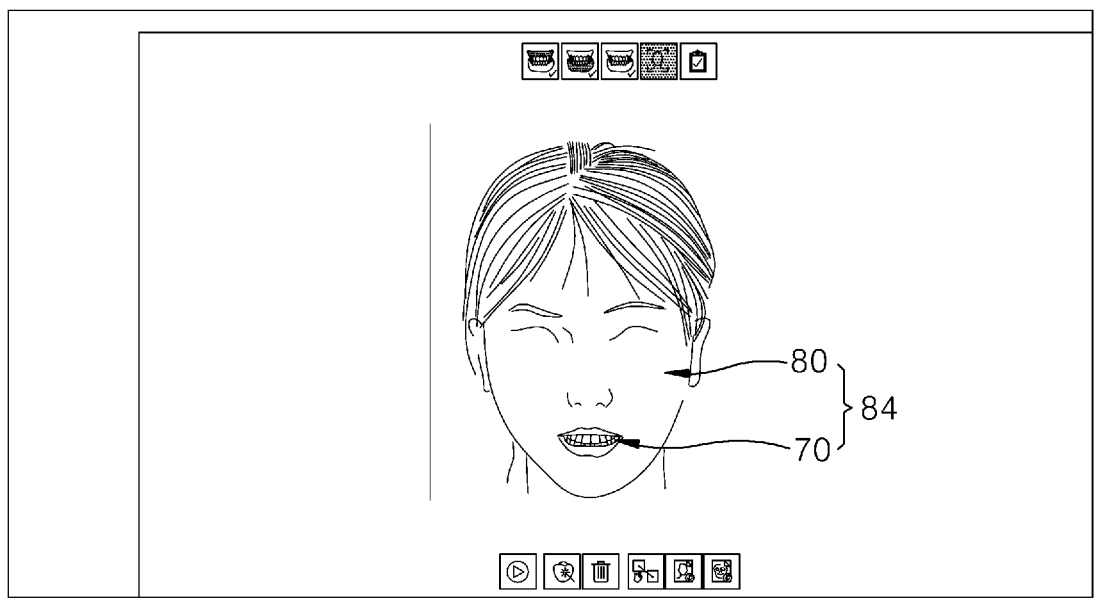

Referring to FIGS. 15 to 21, first, as shown in FIGS. 18 and 19, the teeth may be removed from the three-dimensional face scan data 80 corresponding to the second facial data (the facial data acquired by the oral scanner) using a standard trimming tool. Next, when corresponding points 72 and 82 corresponding to a nose part, teeth part, gum part, lips part, philtrum part, and the like of the patient, respectively, are points designated in the data 70 in which the occlusal oral data and the first facial data have been matched and the three-dimensional face scan data 80, the third matching unit 138 may generate the three-dimensional model 84 in which the three-dimensional face scan data 80 (the second facial data) and the oral data 70 have been matched by matching the two data by the ICP method or the like using the designated corresponding points 72 and 82.

Figure 22:
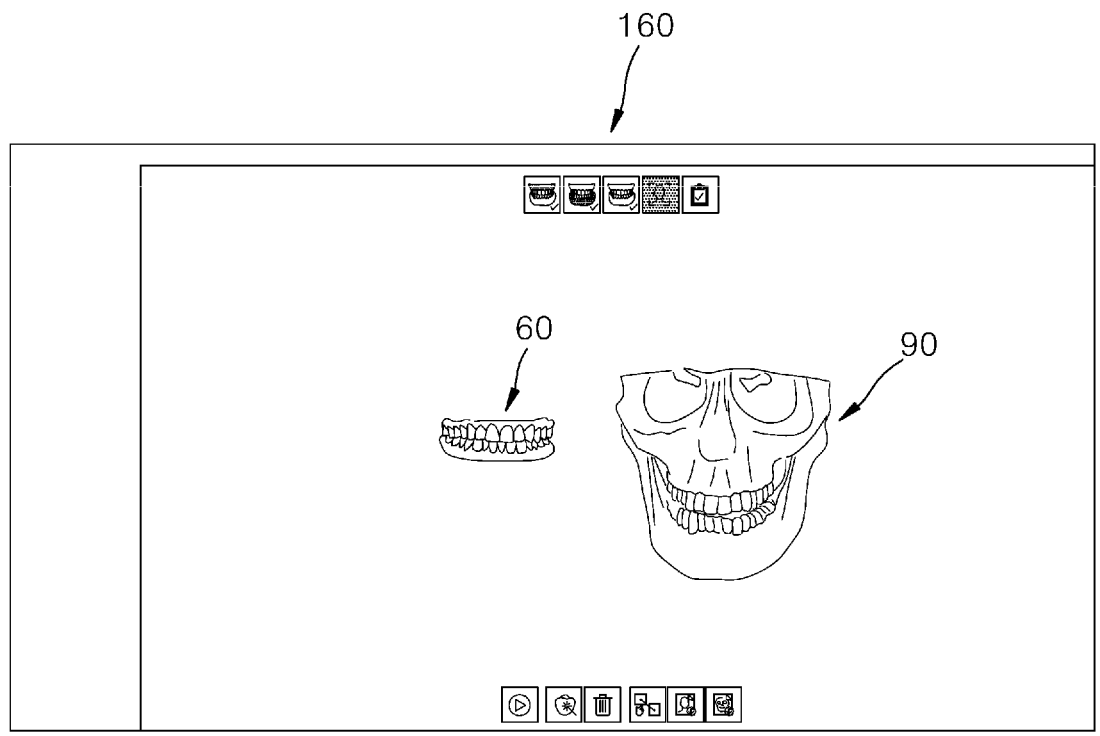
FIG. 22 is an exemplary view showing a screen on which oral data and CT data have been selected according to the embodiment of the present disclosure.
Figure 23:
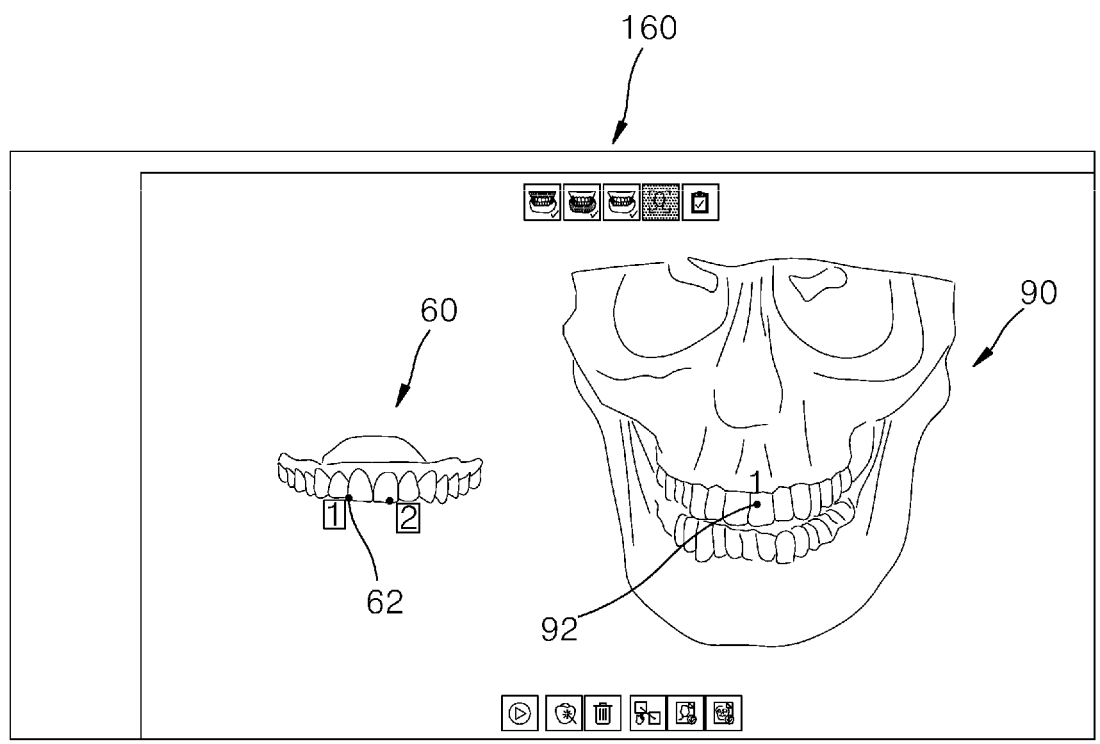
FIGS. 23 and 24 are exemplary views for describing a process of matching the oral data with the CT data according to the embodiment of the present disclosure.
Figure 24:
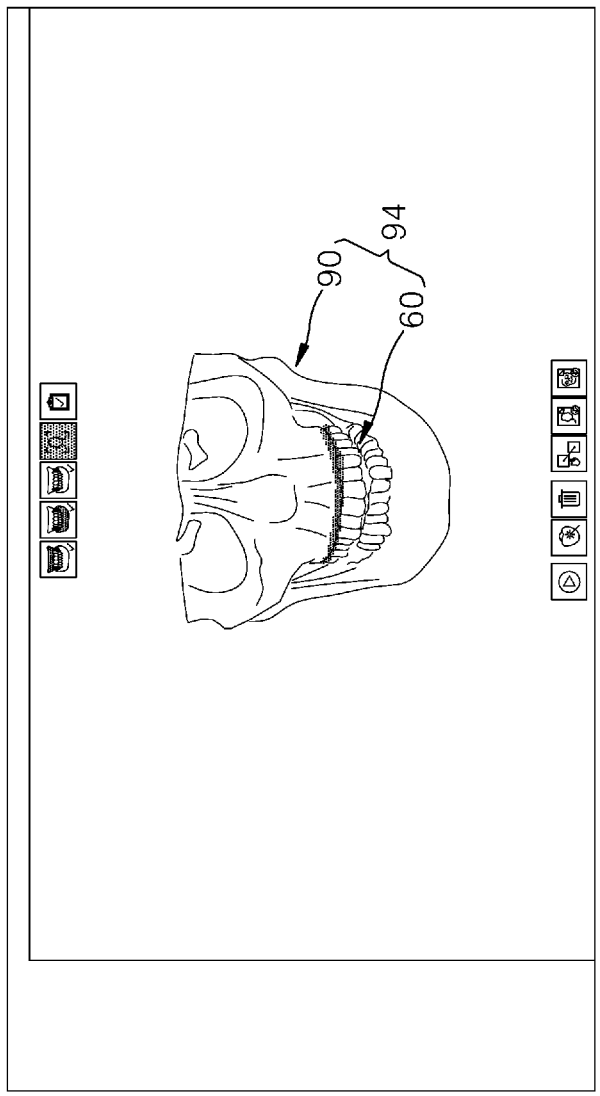

FIG. 22 is an exemplary view showing a screen on which oral data and CT data have been selected according to the embodiment of the present disclosure. FIGS. 23 and 24 are exemplary views for describing a process of matching the oral data with the CT data according to the embodiment of the present disclosure. The embodiment of FIGS. 22 to 24 show an example in which the CT data 90 is selected as the second facial data, and the maxillary oral data is selected as the oral data 60.

Referring to FIGS. 15 and 22 to 24, when corresponding points 62 and 92 corresponding to the teeth parts, respectively are points designated in the oral data and the CT data 90, the third matching unit 138 may generate a three-dimensional model 94 in which the CT data (the second facial data) and the oral data 60 have been matched by matching the two data by the ICP method or the like using the designated corresponding points 62 and 92.

The embodiment of FIGS. 15 to 24 may provide the integrated three-dimensional data for the entire face area of the patient such as the patient's face or facial bone as well as teeth/gums by additionally providing information such as the three-dimensional facial scan data obtained by scanning the entire face of the patient or the CT data together with the oral data for the patient's affected area acquired by the oral scanner. Accordingly, there is an advantage in that it is possible to easily check the states of the shapes of the teeth and the face before treatment during the treatment of diseases and the orthodontic treatment related to teeth and jawbone and easily predict the expected changes after treatment, and the three-dimensional model may be used to determine the insertion direction of the implant or design the prosthesis in consideration of the shapes of the teeth and the face around the missed affected area when planning implant surgery.

The above-described embodiments may be implemented by a hardware component, a software component, and/or a combination of a hardware component and a software component. For example, the apparatus, method, and components described in the embodiments may be implemented by using, for example, one or more general purpose computer or a special purpose computer such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions.

The processing device may run an operating system and one or more software applications running on the operating system. The processing device may also access, store, operate, process, and generate data in response to the execution of the software. For convenience of understanding, there is a case in which one processing device is used, but those skilled in the art will understand that the processing device may include a plurality of processing elements and/or a plurality of types of processing elements.

For example, the processing device may include a plurality of processors or one processor and one controller. In addition, other processing configurations such as a parallel processor are also possible. The software may include computer programs, codes, instructions, or a combination of one or more thereof, and configure the processing device to be operated as desired or instruct the processing device independently or collectively.

The software and/or the data may be permanently or temporarily embodied in any kind of machine, component, physical device, virtual equipment, computer storage medium or device, or a transmitted signal wave in order to be interpreted by the processing device or provide commands or data to the processing device. The software may be distributed over networked computer systems, and may also be stored or executed in a distributed method. The software and the data may be stored in one or more computer-readable recording media.

The method according to the embodiment may be implemented in the form of program instructions that may be executed through various computer means and recorded in a computer-readable medium. The computer-readable medium may include program instructions, data files, data structures, and the like alone or in combination. The program instructions recorded in the medium may be specially designed and configured for the embodiment, or may also be known and available to those skilled in the art of computer software.

Examples of the computer-readable recording medium include magnetic media such as a hard disk, a floppy disk, and a magnetic tape, optical media such as CDROM and DVD, and hardware devices specially configured to store and perform the program instructions such as ROM, RAM, and flash memory. Examples of program instructions include not only machine language codes such as those generated by a compiler, but also high-level language codes that may be executed by a computer using an interpreter or the like. The above-described hardware devices may be configured to be operated as one or more software modules to perform the operations of the embodiments, and vice versa.

As described above, although the embodiments have been described with reference to the limited embodiments and drawings, various modifications and changes are possible by those skilled in the art from the above description. For example, even when the described technologies are performed in an order different from the described method, and/or the described components of the system, structure, apparatus, circuit, and the like are coupled or combined in the forms different from those of the described method, or substituted or replaced with other components and equivalents, appropriate results may be achieved. Accordingly, other implementations, other embodiments, and equivalents to the claims are also included within the scope of the claims to be described below.

INDUSTRIAL APPLICABILITY

The present disclosure provides the apparatus and method for generating the three-dimensional model through data matching, which provide information that enables more accurate treatment for prosthesis manufacturing or orthodontics through multiple data matching based on the facial data, maxillary/mandibular oral data, and occlusal oral data of the patient acquired by the oral scanner, and the recoding medium.

The invention claimed is:

1. A method of generating a three-dimensional model through data matching, the method comprising:
    a maxilla scanning operation of acquiring maxillary oral data including maxillary teeth by scanning a patient's maxilla using an oral scanner;
    a mandible scanning operation of acquiring mandibular oral data including mandible teeth by scanning the patient's mandible using the oral scanner;
    an occluding operation of acquiring occlusal oral data in a state in which the maxillary teeth and the mandibular teeth have been occluded using the oral scanner;
    a face scanning operation of acquiring first facial data by scanning a part of the patient's entire face using the oral scanner so that the patient's nose and a part of the patient's teeth is included in a facial area for a part of a front portion of an oral cavity; and
    a matching operation of matching the first facial data with at least one among the maxillary oral data, the mandibular oral data, and the occlusal oral data,
    wherein an oral data including the maxillary oral data, the mandibular oral data, and the occlusal oral data, and the first facial data are acquired through the oral scanner,
    wherein in the matching operation, the first facial data and the oral data are matched by designating a point of a teeth part to be matched with the oral data in the first facial data, and by designating a point at a position corresponding to the point designated in the first facial data in the oral data, wherein data that the oral data and the first facial data are matched, and second facial data obtained by scanning the entire face of the patient are matched by designated points of a nose part respectively, wherein the point is at least one of points on a surface of a three-dimensional surface data.

2. The method of claim 1,
wherein the matching operation includes:
a teeth data extracting operation of extracting teeth data corresponding to a part of the patient's teeth from the first facial data;
a first matching operation of matching the teeth data with at least one of the maxillary oral data and the mandibular oral data; and
a second matching operation of matching the occlusal oral data with the first facial data based on matching information of the teeth data and the oral data.

3. The method of claim 1,
wherein the first facial data is acquired by scanning a facial area including lips and philtrum between the patient's nose and a part of teeth.

4. The method of claim 1,
wherein the matching operation includes an operation of matching second facial data including at least one of three-dimensional face scan data obtained by scanning the entire face of the patient and CT data with oral data including at least one among the maxillary oral data, the mandibular oral data, and the occlusal oral data.

5. The method of claim 4,
wherein the oral data including the at least one among the maxillary oral data, the mandibular oral data, and the occlusal oral data is matched with the second facial data using the patient's nose.

6. A non-transitory computer-readable recording medium in which a program for executing the method of generating the three-dimensional model for data matching of claim 1 is recorded.

7. An apparatus for generating a three-dimensional model through data matching, the apparatus comprising:
an oral scanner configured to acquire maxillary oral data by scanning a patient's maxillary teeth, acquire mandibular oral data by scanning mandibular teeth of the patient, acquire teeth scan data by scanning a part of the patient's teeth in a state in which the maxillary teeth and the mandibular teeth have been occluded, and acquire first facial data by scanning a part of the patient's entire face so that the patient's nose and a part of the patient's teeth is included in a facial area for a part of a front portion of an oral cavity;
an occlusion unit configured to acquire occlusal oral data in a state in which the maxillary oral data and the mandibular oral data have been occluded using the teeth scan data; and
a matching unit configured to match the first facial data with at least one among the maxillary oral data, the mandibular oral data, and the occlusal oral data, wherein an oral data including the maxillary oral data, the mandibular oral data, and the occlusal oral data, and the first facial data are acquired through the oral scanner, wherein the matching unit matches the first facial data and the oral data by designating a point of a teeth part to be matched with the oral data in the first facial data, and by designating a point at a position corresponding to the point designated in the first facial data in the oral data, wherein the matching unit matches data that the oral data and the first facial data are matched, and second facial data obtained by scanning the entire face of the patient are matched by designating points of a nose part respectively, and wherein the point is at least one of points on a surface of a three-dimensional surface data.

8. The apparatus of claim 7,
wherein the matching unit includes:
a teeth data extraction unit configured to extract teeth data corresponding to a part of the patient's teeth from the first facial data;
a first matching unit configured to match the teeth data with at least one of the maxillary oral data and the mandibular oral data; and
a second matching unit configured to match the occlusal oral data with the first facial data based on matching information of the teeth data and the oral data.

9. The apparatus of claim 8,
wherein the first facial data is acquired by scanning the facial area including lips and philtrum between the nose and a part of teeth of the patient.

10. The apparatus of claim 7,
wherein the matching unit matches second facial data including at least one of three-dimensional face scan data obtained by scanning the entire face of the patient and CT data with oral data including at least one among the maxillary oral data, the mandibular oral data, and the occlusal oral data.

11. The apparatus of claim 10,
wherein the matching unit matches the oral data including at least one among the maxillary oral data, the mandibular oral data, and the occlusal oral data with the second facial data using the patient's nose.

* * * * *